US012600998B2

(12) United States Patent
Abysalh et al.

(10) Patent No.: US 12,600,998 B2
(45) Date of Patent: Apr. 14, 2026

(54) LARGE SCALE SYNTHESIS OF MESSENGER RNA

(71) Applicant: Translate Bio, Inc., Lexington, MA (US)

(72) Inventors: Jonathan Abysalh, Lexington, MA (US); Anusha Dias, Lexington, MA (US); Jorel E. Vargas, Lexington, MA (US); Dustin Cooper, Lexington, MA (US); Frank DeRosa, Lexington, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 83 days.

(21) Appl. No.: 17/502,816

(22) Filed: Oct. 15, 2021

(65) Prior Publication Data

US 2022/0136022 A1 May 5, 2022

Related U.S. Application Data

(60) Provisional application No. 63/092,274, filed on Oct. 15, 2020.

(51) Int. Cl.
*C12P 19/34* (2006.01)
*A61K 31/713* (2006.01)
(52) U.S. Cl.
CPC ............ *C12P 19/34* (2013.01); *A61K 31/713* (2013.01)
(58) Field of Classification Search
CPC ............ C12N 15/1003; C12N 2330/30; C12N 9/1247; C12P 19/34; C07H 21/02; A61K 31/713
See application file for complete search history.

(56) References Cited

U.S. PATENT DOCUMENTS

| 11,253,605 B2* | 2/2022 | Dias | ................... | A61K 31/7105 |
| 11,560,562 B2* | 1/2023 | Dias | ................ | G01N 27/44778 |

(Continued)

FOREIGN PATENT DOCUMENTS

| CN | 111212905 A | 5/2020 |
| TW | 202023580 A | 7/2020 |

(Continued)

OTHER PUBLICATIONS

"Between" definition provided by Merriam Webster's Dictionary, downloaded from https://www.merriam-webster.com/dictionary on Nov. 4, 2023.*

(Continued)

*Primary Examiner* — Terra C Gibbs
(74) *Attorney, Agent, or Firm* — LATHROP GPM LLP; James H. Velema, Esq.

(57) ABSTRACT

The present invention provides, among other things, methods for large-scale production of a composition comprising full-length messenger RNA product that is substantially free of double-stranded RNA, and compositions produced using such methods and uses thereof. The present invention is based, in part, on the surprising discovery that mRNA product produced by in vitro transcription using an SP6 RNA polymerase is substantially free of double-stranded RNA. In one aspect, the present invention provides methods of generating large-scale mRNA product for mRNA therapy without need for a chromatography step.

19 Claims, 11 Drawing Sheets

Specification includes a Sequence Listing.

(a)    ⟵ AUU $^{U}$A
...GUAGAGGUGA $_{A}$G    (SEQ ID NO: 14)

(b)    ⟵ AUUUAGAAGUGGAGAUG...5′ (SEQ ID NO: 16)
5′...GCUGACUGUAUCUUC...3′ (SEQ ID NO: 15)

(c)    ⟵ CAUGG    (SEQ ID NO: 18)
5′...GUAGAGGUGAGUACCGUACG....3′ (SEQ ID NO: 17)

(56)     References Cited

U.S. PATENT DOCUMENTS

| | | |
|---|---|---|
| 2016/0326575 A1 | 11/2016 | Von Der Mulbe et al. |
| 2018/0161451 A1 | 6/2018 | Fotin-Mleczek et al. |
| 2018/0258423 A1 | 9/2018 | Dias et al. |

FOREIGN PATENT DOCUMENTS

| | | |
|---|---|---|
| WO | WO 2012/170930 A1 | 12/2012 |
| WO | WO 2015/188933 A1 | 12/2015 |
| WO | WO 2016/149508 A1 | 9/2016 |
| WO | WO 2016/180430 A1 | 11/2016 |
| WO | WO 2018/053209 A1 | 3/2018 |
| WO | WO 2018/157153 A1 | 8/2018 |
| WO | WO 2018/157154 A2 | 8/2018 |
| WO | WO 2019/036682 A1 | 2/2019 |
| WO | WO 2019/207060 A1 | 10/2019 |
| WO | WO 2020/023888 A2 | 1/2020 |

OTHER PUBLICATIONS

"About" definition provided by Merriam Webster's Dictionary, downloaded from https://www.merriam-webster.com/dictionary on Nov. 4, 2023.*

Stump et al. (Nucleic Acids Research, 1993 vol. 21:5480-5484).*

Alton, E. et al., "A randomised, double-blind, placebo-controlled trial of repeated nebulisation of non-viral cystic fibrosis transmembrane conductance regulator (CFTR) gene therapy in patients with cystic fibrosis," Efficacy and Mechanism Evaluation, Jul. 2016, vol. 3, No. 5, ISSN 2050-4365.

Anonymous, "RiboMAX™ Large Scale RNA Production Systems-SP6 and T7", Promega, pp. 1-14 (2017).

Brito et al., "Self-Amplifying mRNA Vaccines", Advances in Genetics, 89: 179-233 (2015).

Gonzalez-Perez et al., "Scaling up in vitro transcription synthesis of RNA standards for competitive quantitative RT-PCR: Looking for bigger yields", Anal Biochem., 385(1): 179-81 (2009).

Gurevich et al., "Preparative in vitro mRNA Synthesis Using SP6 and T7 RNA Polymerases", Analytical Biochemistry, 195: 207-213 (1991).

He et al., "Rapid Mutagensis and Purification of Phage RNA Polymerases", Protein Expression and Purification, 9: 142-151 (1997).

International Preliminary Report on Patentability for PCT/US2018/020008, 7 pages, (dated Sep. 6, 2019).

International Search Report and Written Opinion for PCT/US2018/020008, 18 pages, (dated May 11, 2018).

Krieg et al., "In Vitro RNA Synthesis with SP6 RNA Polymerase", Methods in Enzymology, 155: 397-415 (1987).

Lee et al., "Tiny abortive initiation transcripts exert antitermination activity on an RNA hairpin-dependent intrinsic terminator", Nucleic Acids Research, vol. 38, No. 18, pp. 6045-6053 (2010).

Pascolo, S., "Vaccination with messenger RNA", Methods in Molecular Medicine; 127: 23-40 (2006).

Robinson et al., "Lipid Nanoparticle-Delivered Chemically Modified mRNA Restores Chloride Secretion in Cystic Fibrosis", Molecular Therapy, 26(8): 1-13 (2018).

Skeidsvoll et al., "Analysis of RNA by capillary electrophoresis", Electrophoresis, 17: 1512-1517 (1996).

Thurston et al., "Electrophoresis of RNA Denatured with Glyoxal or Formaldehyde", Methods in Molecular Biology, 4: 1-11 (1988).

Yang et al., "Determination of RNA degradation by capillary electrophoresis with cyan light-emitted diode-induced fluorescence", Journal of Chromatography A 2012; 1239: 78-84 (2012).

Yoshioka et al., "Efficient generation of human iPSCs by a synthetic self-replicative RNA", Cell Stem Cell, 13(2): 246-54 (2013).

International Search Report and Written Opinion for PCT/US2021/055221 dated Feb. 3, 2022 (12 pages).

* cited by examiner

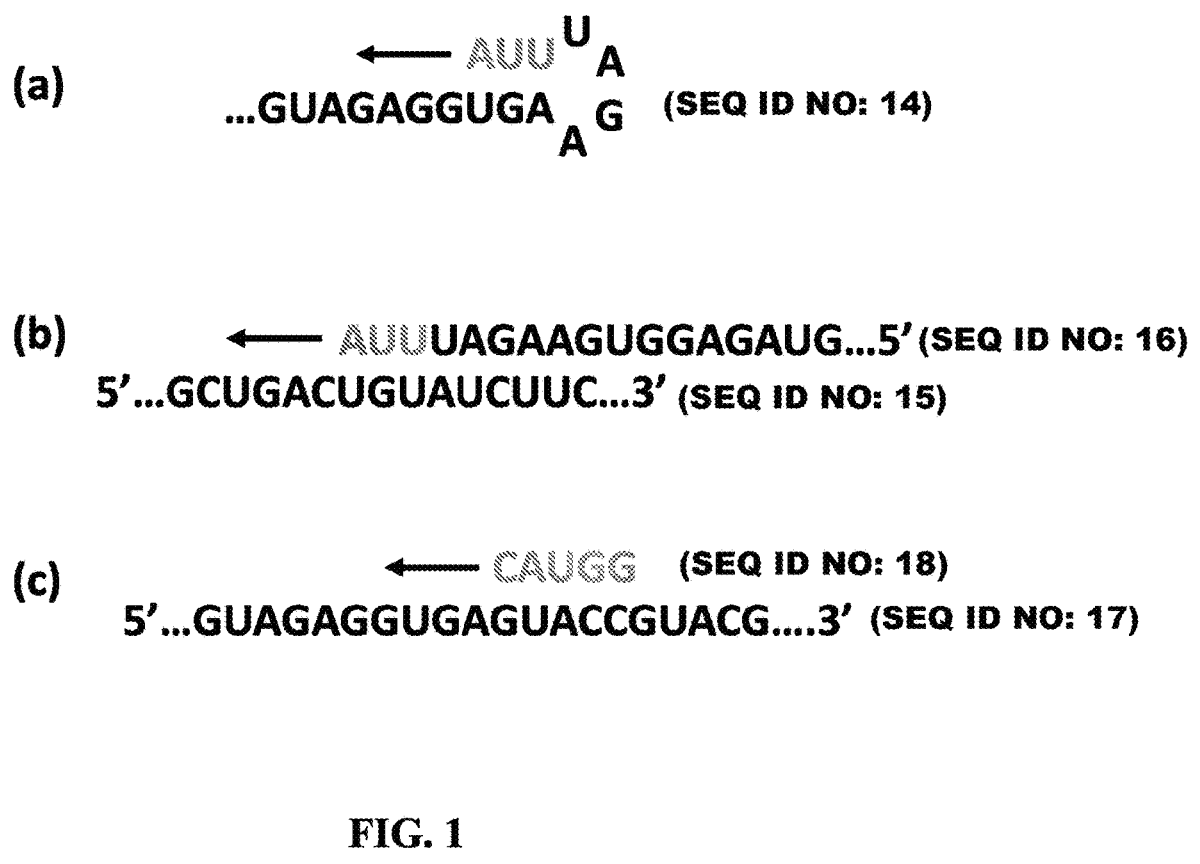

(a)

$$\longleftarrow \text{AUU} \begin{smallmatrix} \text{U} \\ \text{A} \end{smallmatrix}$$

...GUAGAGGUGA $\begin{smallmatrix} \\ \text{A} \end{smallmatrix}$ G    (SEQ ID NO: 14)

(b)

$\longleftarrow$ AUUUAGAAGUGGAGAUG...5' (SEQ ID NO: 16)

5'...GCUGACUGUAUCUUC...3' (SEQ ID NO: 15)

(c)

$\longleftarrow$ CAUGG    (SEQ ID NO: 18)

5'...GUAGAGGUGAGUACCGUACG....3' (SEQ ID NO: 17)

FIG. 1

Tail Length and Integrity (CE)

OTC IVT
main peak ~94%

OTC mRNA
main peak ~91%
tail length ~ 172nt mRNA Cap Analysis (UPLC-MS)

| CAP Species | OTC (%) | Standard (%) |
|---|---|---|
| Uncapped | 6.9 | 26.4 |
| Cap 0 | 0.0 | 25.0 |
| Cap G | 0.0 | 22.1 |
| Cap 1 | 93.1 | 26.5 |

LARGE SCALE SYNTHESIS OF MESSENGER RNA

CROSS-REFERENCE TO RELATED APPLICATION

This application claims benefit of U.S. Provisional Application No. 63/092,274, filed on Oct. 15, 2020, the entire disclosure of which is hereby incorporated by reference.

SEQUENCE LISTING

The present specification makes reference to a Sequence Listing (submitted electronically as a .txt file named "MRT-2150US1_Sequence listing_ST25." The .txt file was generated on Nov. 30, 2021 and is 14 kb in size. The entire contents of the Sequence Listing are herein incorporated by reference.

BACKGROUND OF THE INVENTION

Messenger RNA (mRNA) therapy is becoming an increasingly important approach for the treatment of a variety of diseases. mRNA therapy involves administration of a drug product comprising in vitro transcribed (IVT) and highly pure messenger RNA (mRNA) into a patient in need of the therapy and production of the protein encoded by the mRNA within the patient's body.

Production of mRNA by in vitro transcription also generates double-stranded RNA (dsRNA), which is a major contaminant in mRNA product that would not be acceptable for mRNA therapy. Double-stranded RNA is undesirable since it leads to inefficient translation of the administered mRNA product and results in induction of cytokines, triggering an immune response.

Traditionally, mRNA generated from in vitro transcription is purified using commercially-available chromatography systems, and/or by extraction into an organic mix (phenol: chloroform:isoamyl alcohol) and subsequent ethanol precipitation. However, the dsRNA impurities are not efficiently removed by standard purification methods, including lithium chloride or alcohol-based precipitation, size exclusion and ion exchange chromatography, or purification based on silica matrices.

The dsRNA impurities can be removed only by procedures requiring special instrumentation and generating hazardous waste. Currently, ion pair reversed-phase high-performance liquid chromatography (HPLC) is the method used to eliminate dsRNA contaminants from long IVT mRNAs. However, this method is expensive, not scalable, and employs toxic acetonitrile.

SUMMARY OF THE INVENTION

There is a need for a cost-effective large-scale synthesis method for producing highly pure mRNA product that lacks contaminating double-stranded RNA (dsRNA), suitable for mRNA therapeutics. The present invention provides, among other things, a large-scale in vitro synthesis method that produces mRNA lacking or substantially free of contaminating dsRNA. The present invention provides, among other things, a method of generating mRNA product using SP6 RNA Polymerase without a need for a post-synthesis purification step, such as chromatographic methods (e.g., ion pair reversed-phase high-performance liquid chromatography or size exclusion and ion exchange chromatography), to remove contaminating dsRNA.

The invention is based, in part, upon the surprising discovery that SP6 RNA Polymerase synthesizes full-length mRNA with significantly reduced dsRNA as compared to other RNA polymerases, such as T7 RNA polymerase. As described in more detail below, including the Examples section, mRNA product synthesized by an SP6 RNA polymerase is high yielding and is substantially free of dsRNA as compared to the mRNA product synthesized by a T7 RNA polymerase. The mRNA product generated through IVT by SP6 RNA polymerase is not only enriched in full length mRNA with substantially reduced abortive transcripts, but also has the surprising and unexpected property of being substantially free of dsRNA. These unique and advantageous properties of SP6 RNA polymerase yield mRNA product of a significantly higher quality suitable for mRNA therapeutics, as compared to mRNA product generated by T7 RNA polymerase. Accordingly, the present invention provides, in part, a method of synthesizing in vitro mRNA without the need for post-synthesis purification methods, including, for example, the chromatographic methods (e.g., those mentioned above and in the background of the invention) to remove dsRNA.

If necessary, the in vitro synthesized mRNA produced by a method of the invention can be purified to remove contaminants that derive from the in vitro synthesis reaction (such as the one or more enzyme(s) used in that reaction), e.g., by precipitation- and filtration-based processes that can be operated with batches of in vitro synthesized mRNA of 1 gram or more. Such processes may involve, e.g., tangential flow filtration, depth filtration, or centrifugation (e.g., using a filtering centrifuge). Suitable processes are described, e.g., in WO 2015/164773, WO 2018/157141 and WO 2020/041793.

In one aspect, the present invention provides a method of large-scale production of a composition comprising full-length messenger RNA (mRNA), comprising synthesizing in vitro mRNA using an SP6 RNA polymerase, wherein at least 1 gram (1 g) of mRNA is synthesized in a single batch and wherein the composition contains less than 1% of double-stranded RNA (dsRNA) by weight.

In some embodiments, the method does not comprise a chromatography step.

In some embodiments, the entire method is performed in non-denaturing conditions. In some embodiments, the mRNA is synthesized at a non-denaturing condition.

In one aspect, the invention provides a method of producing a composition comprising full-length messenger RNA (mRNA), comprising synthesizing in vitro mRNA, wherein the composition contains less than 1% of double-stranded RNA (dsRNA) by weight, and wherein the method does not comprise a chromatography step.

In one aspect, the present invention provides a method of producing a composition comprising full-length messenger RNA (mRNA), comprising synthesizing in vitro mRNA, wherein the composition contains less than 1% of double-stranded RNA (dsRNA) by weight, and wherein the mRNA is synthesized at a non-denaturing condition.

In some embodiments, the method comprises synthesizing in vitro mRNA, wherein at least 1 g of mRNA is synthesized in a single batch.

In some embodiments, the method comprises synthesizing in vitro mRNA, wherein at least 10 g, 100 g, 250 g, 500 g, 1 kg, or 10 kg of mRNA is synthesized in the single batch. Accordingly, in some embodiments, the method comprises synthesizing in vitro mRNA, wherein at least 10 g of mRNA is synthesized. In some embodiments, in some embodiments, the method comprises synthesizing in vitro mRNA, wherein at least 100 g of mRNA is synthesized. In some embodiments, in some embodiments, the method comprises synthesizing in vitro mRNA, wherein at least 500 g of mRNA is synthesized. In some embodiments, in some embodiments, the method comprises synthesizing in vitro mRNA, wherein at least 1 kg of mRNA is synthesized. In some embodiments, in some embodiments, the method comprises synthesizing in vitro mRNA, wherein at least 10 kg of mRNA is synthesized. In some embodiments, the method comprises synthesizes in vitro mRNA, wherein more than 10 kg of mRNA is synthesized in a single batch. For example, in some embodiments, 25 kg, 50 kg, 75 kg, 100 kg or more of in vitro synthesized mRNA is synthesized in a single batch.

In some embodiments, the method comprises synthesizing in vitro mRNA, wherein the composition contains less than 0.9%, 0.8%, 0.7%, 0.6%, 0.5%, 0.4%, 0.3%, 0.2% 0.10%, 0.05%, 0.010% of the dsRNA by weight.

In some embodiments, the method comprises synthesizing in vitro mRNA wherein the composition is substantially free of the dsRNA.

In some embodiments, the method comprises synthesizing in vitro mRNA, wherein the in vitro synthesis of mRNA is performed at pH between about 6 to 8.5, between about 6.5 to 8.0 or between about 7.0 to 7.5. In particular embodiments, the in vitro synthesis of mRNA is performed at pH is between 7.5 and 7.7. In some embodiments, the pH is 6, 6.2, 6.4, 6.8, 7.0, 7.2, 7.4, 7.6, 7.8, 8.0, 8.2 or 8.4. In some embodiments, the pH is 7.5. In some embodiments, the pH is 7.7.

In some embodiments, the method comprises synthesizing in vitro mRNA, wherein the in vitro synthesis of mRNA is performed in a buffer comprising 25 mM tris HCl, 2 mM spermidine, 25 mM MgCl, 0.5 mM NaCl, and pH 7.5.

In some embodiments, the method comprises synthesizing in vitro mRNA, wherein the method does not comprise a chaotropic agent. Chaotropic agents are substances which disrupt the structure of macromolecules such as proteins and nucleic acids by interfering with non-covalent forces such as hydrogen bonds and van der Waals forces. In some embodiments, a chaotropic agent, include for example, urea, thiourea, guanidinium chloride, guanidinium thiocyanate, guanidinium isothiocyanate, lithium acetate, magnesium chloride, sodium dodecyl sulfate, lithium perchlorate and combination thereof.

In one aspect, the present invention provides a method of large-scale production of a composition comprising full-length messenger RNA (mRNA), comprising synthesizing in vitro mRNA using an SP6 RNA polymerase, wherein the composition comprises less than 1% of double-stranded RNA (dsRNA) by weight, and wherein at least 100 mg of mRNA is synthesized in a single batch.

In some embodiments, the composition contains less than 0.9%, 0.8%, 0.7%, 0.6%, 0.5%, 0.4%, 0.3%, 0.2%, 0.1%, 0.05%, 0.01% of the dsRNA by weight.

In some embodiments, the composition is substantially free of the dsRNA.

In some embodiments, the dsRNA is detected by dot blot assay or ELISA.

In some embodiments, the dsRNA is detected prior to capping or tailing the synthesized mRNA.

In some embodiments, the method further comprises a step of capping and/or tailing the synthesized mRNA.

In some embodiments, the dsRNA is detected after capping and tailing of the synthesized mRNA.

In some embodiments, at least 200 mg, 300 mg, 400 mg, 500 mg, 600 mg, 700 mg, 800 mg, 900 mg, 1 g, 5 g, 10 g, 25 g, 50 g, 75 g, 100 g, 150 g, 200 g, 250 g, 500 g, 750 g, 1 kg, 5 kg, 10 kg, or more of mRNA is synthesized in a single batch. In a typical embodiment, 1 g to 100 kg of mRNA (e.g., 100 g to 10 kg, or 250 g to 5 kg) is synthesized in a single batch. In some embodiments, 10 kg mRNA or more is synthesized in a single batch. In particular embodiments, between 10 kg and 100 kg of mRNA is synthesized in a single batch. In some embodiments, 15 kg, 20 kg, 25 kg, 30 kg, 35 kg, 40 kg, 45 kg, 50 kg, 75 kg or 100 kg or more of mRNA is synthesize in a single batch.

In some embodiments, the method does not include a step of specifically removing the dsRNA.

In some embodiments, the method does not comprise a chromatography step.

In some embodiments, the SP6 RNA polymerase is a naturally occurring SP6 RNA polymerase.

In some embodiments, the SP6 RNA polymerase is a recombinant SP6 RNA polymerase.

In some embodiments, the SP6 RNA polymerase comprises a tag. In some embodiments, the tag is a his-tag.

In some embodiments, the mRNA is synthesized by the SP6 RNA polymerase based on a DNA template, e.g., a DNA template including an SP6 promoter operably linked to a DNA sequence encoding the mRNA sequence to be synthesized. In some embodiments, the DNA sequence is optimized. In some embodiments, the DNA sequence is optimized to reduce the chance of a hairpin structure forming in the synthesized mRNA.

In some embodiments, the amount of SP6 RNA polymerase by weight in a reaction mixture is equal to or greater than the amount of DNA template by weight. In a particular embodiment, the weight ratio of DNA template to SP6 RNA polymerase is between 1:1 and 1:3. In some embodiments, the amount of SP6 RNA polymerase is adjusted relative to the amount of DNA template in a reaction condition in order to achieve a desired yield. For example, in some embodiments, the amount of SP6 RNA polymerase is increased relative to the amount of DNA template.

In some embodiments, the mRNA is synthesized in a reaction mixture comprising NTPs at a concentration ranging from 1-10 mM (e.g., 1-8 mM, 1-6 mM, 1-5 mM, 2-10 mM, 2-8 mM, 2-6 mM, and 4-5 mM) for each NTP, the DNA template at a concentration ranging from 0.01-0.5 mg/mL (e.g., 0.05-0.4 mg/mL, 0.05-0.3 mg/mL, 0.05-0.2 mg/mL, and 0.05-0.15 mg/mL), and the SP6 RNA polymerase at a concentration ranging from 0.01-0.1 mg/mL (e.g., 0.02-0.08 mg/mL, and 0.04-0.06 mg/mL).

In some embodiments, the reaction mixture comprises NTPs at a concentration of 5 mM each NTP, the DNA template at a concentration of 0.1 mg/mL, and the SP6 RNA polymerase at a concentration of 0.05 mg/mL.

In some embodiments, the mRNA is synthesized at a temperature ranging from 37-42° C. In some embodiments, the mRNA is synthesized at a temperature of about 37° C., 38° C., 39° C., 40° C., 41° C., 42° C. or 45° C.

In some embodiments, the NTPs are naturally-occurring NTPs. In some embodiments, the NTPs comprise modified NTPs. In some embodiments, the modified NTPs comprise pseudouridine. In more specific embodiments, pseudouridine is N-1-methyl-pseudouridine).

In some embodiments, the mRNA encodes human Cystic Fibrosis Transmembrane Conductance Regulator (CFTR).

In some embodiments, the mRNA encodes human Ornithine Transcarbamylase (OTC).

In some embodiments, the full-length mRNA molecule is at least 100 bases, 200 bases, 300 bases, 400 bases, 500 bases, 600 bases, 700 bases, 800 bases, 900 bases, 1 kb, 1.5 kb, 2 kb, 2.5 kb, 3 kb, 3.5 kb, 4 kb, 4.5 kb, 5 kb, 8 kb, 10 kb, or 15 kb in length.

In some embodiments, the mRNA is codon optimized.

In some embodiments, provided is a composition comprising mRNA produced by the methods of the present invention.

In one aspect, the present invention provides a composition comprising in vitro synthesized messenger RNA (mRNA) produced in a single batch using SP6 RNA polymerase without purification by a chromatography step, wherein the composition contains less than 1% of double-stranded RNA (dsRNA).

In some embodiments, the composition comprises at least 100 mg, 200 mg, 300 mg, 400 mg, 500 mg, 600 mg, 700 mg, 800 mg, 900 mg, 1 g, 5 g, 10 g, 25 g, 50 g, 75 g, 100 g, 150 g, 200 g, 250 g, 500 g, 750 g, 1 kg, 5 kg, 10 kg, or more of mRNA. In a typical embodiment, the composition comprises 1 g to 100 kg of mRNA (e.g., 100 g to 10 kg, or 250 g to 5 kg). In some embodiments, the composition comprises 10 kg mRNA or more. In particular embodiments, the composition comprises between 10 kg and 100 kg of mRNA. For example, in some embodiments, the composition comprises 15 kg, 20 kg, 25 kg, 30 kg, 35 kg, 40 kg, 45 kg, 50 kg, 75 kg or 100 kg or more of mRNA.

In some embodiments, the present invention provides a composition, wherein the mRNA is synthesized using an SP6 RNA polymerase.

In some embodiments, the composition comprises less than 0.9%, 0.8%, 0.7%, 0.6%, 0.5%, 0.4%, 0.3%, 0.2% 0.1%, 0.05%, 0.01% of the dsRNA by weight. Accordingly, in some embodiments, the composition comprises less than 0.9% of the dsRNA by weight. In some embodiments, the composition comprises less than 0.8% of the dsRNA by weight. In some embodiments, the composition comprises less than 0.7% of the dsRNA by weight. In some embodiments, the composition comprises less than 0.6% of the dsRNA by weight. In some embodiments, the composition comprises less than 0.5% of the dsRNA by weight. In some embodiments, the composition comprises less than 0.4% of the dsRNA by weight. In some embodiments, the composition comprises less than 0.3% of the dsRNA by weight. In some embodiments, the composition comprises less than 0.2% of the dsRNA by weight. In some embodiments, the composition comprises less than 0.10% of the dsRNA by weight. In some embodiments, the composition comprises less than 0.05% of the dsRNA by weight. In some embodiments, the composition comprises less than 0.01% of the dsRNA by weight.

In some embodiments, the composition is substantially free of the dsRNA. In some embodiments, the composition is substantially free of shortmer contamination. In further embodiments, the composition is substantially free of both dsRNA and shortmer contamination.

In some embodiments, the dsRNA is detected by a dot blot assay.

In some embodiments, the mRNA encodes human Cystic Fibrosis Transmembrane Conductance Regulator (CFTR).

In some embodiments, the mRNA encodes human Ornithine Transcarbamylase (OTC).

In some embodiments, the mRNA is codon optimized. In some embodiments, the mRNA is unmodified. In some embodiments, the mRNA is modified. In certain embodiments, the modified mRNA comprises pseudouridine. In more specific embodiments, pseudouridine is N-1-methyl-pseudouridine).

In some embodiments, the mRNA is at least 100 bases, 200 bases, 300 bases, 400 bases, 500 bases, 600 bases, 700 bases, 800 bases, 900 bases, 1 kb, 1.5 kb, 2 kb, 2.5 kb, 3 kb, 3.5 kb, 4 kb, 4.5 kb, 5 kb, 8 kb, 10 kb, or 15 kb in length.

In some embodiments, the mRNA is encapsulated within a liposome.

In some embodiments, the liposome comprises one or more cationic lipids, one or more non-cationic lipids, and one or more PEG-modified lipids.

In some embodiments, the liposome further comprises cholesterol-based lipids.

In one aspect, a method of treating a disease or disorder is provided comprising use of the composition as described herein.

Any aspect or embodiment described herein can be combined with any other aspect or embodiment as disclosed herein. While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

Other features and advantages of the invention will be apparent from the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWINGS

The following figures are for illustration purposes only and not for limitation.

FIG. 1 is a schematic illustrating the process of dsRNA generation during in vitro transcription. (a) The full-length RNA can form loops with internal regions of complementarity. (b) Abortive RNA fragments generated during the initiation phase of IVT, and the 3' end of the full-length RNA can prime complementary RNA synthesis from the primary transcripts that leads to the generation of dsRNA contaminant. (c) Promoter-independent transcription of full-length anti-sense RNA is another mechanism of dsRNA generation.

FIG. 7A is a graph that depicts the yield of OTC mRNA produced using either Condition A or Condition B. FIG. 7B is a graph that depicts the reagent amounts used with either Condition A or Condition B. FIG. 7C is a graph that illustrates the resultant Cost of Good Produced (CoGS) using either Condition A or Condition B to synthesize mRNA.

DEFINITIONS

Figure 2:
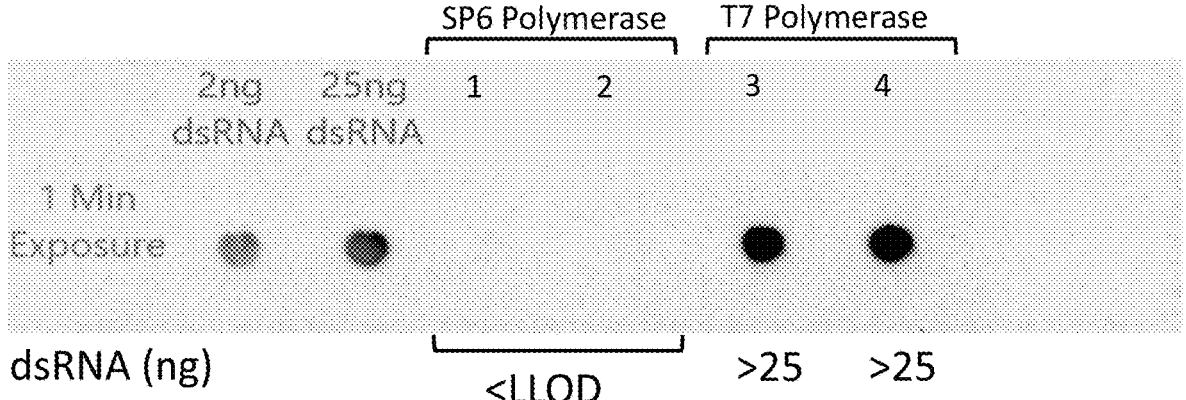
FIG. 2 is a dot blot showing a comparison of the amount of dsRNA present in mRNA product generated by in vitro transcription using SP6 RNA Polymerase (lanes labelled 1 and 2) versus T7 polymerase (lanes labelled 3 and 4). The amount of dsRNA present is quantitated relative to a standard dsRNA control of 2 ng or 25 ng.

In order for the present invention to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Unless specifically stated or evident from context, as used herein, the term "about" is understood as within a range of normal tolerance in the art, for example within 2 standard deviations of the mean. "About" can be understood to be within 10%, 9%, 8%, 7%, 6%, 5%, 4%, 3%, 2%, 1%, 0.5%, 0.1%, 0.05%, 0.01%, or 0.001% of the stated value. Unless otherwise clear from the context, all numerical values provided herein reflects normal fluctuations that can be appreciated by a skilled artisan.

As used herein, term "abortive transcript" or "pre-aborted transcript" or the like, in its broadest sense, is any transcript that is shorter than a full-length mRNA molecule encoded by the DNA template. In some embodiments, an abortive transcript may be less than 90% of the length of the full-length mRNA molecule that is transcribed from the target DNA molecule, e.g., less than 80%, 70%, 60%, 50%, 40%, 30%, 20%, 10%, 5%, 1% of the length of the full-length mRNA molecule.

As used herein, the term "batch" refers to a quantity or amount of mRNA synthesized at one time, e.g., produced according to a single manufacturing order during the same cycle of manufacture. A batch may refer to an amount of mRNA synthesized in one reaction that occurs via a single aliquot of enzyme and/or a single aliquot of DNA template for continuous synthesis under one set of conditions. In some embodiments, a batch would include the mRNA produced from a reaction in which not all reagents and/or components are supplemented and/or replenished as the reaction progresses. The term "batch" would not mean mRNA synthesized at different times that are combined to achieve the desired amount.

As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery).

As used herein, the term "double-stranded RNA" or "dsRNA" refers to RNA produced during in vitro transcription comprising two complementary strands of ribonucleic acid base-paired with each other. During IVT, dsRNA is generated in cis by looping of full-length RNA with internal regions of complementarity. In addition, abortive RNA fragments generated during the initiation phase of IVT, and the 3' end of the full-length RNA can prime complementary RNA synthesis from the primary transcripts in trans. Promoter-independent transcription of full-length anti-sense RNA is another mechanism of dsRNA generation.

As used herein, the terms "drug", "medication", "therapeutic", "active agent", "therapeutic compound", "composition", or "compound" are used interchangeably and refer to any chemical entity, pharmaceutical, drug, biological, botanical, and the like that can be used to treat or prevent a disease, illness, condition, or disorder of bodily function. A drug may comprise both known and potentially therapeutic compounds. A drug may be determined to be therapeutic by screening using the screening known to those having ordinary skill in the art. A "known therapeutic compound", "drug", or "medication" refers to a therapeutic compound that has been shown (e.g., through animal trials or prior experience with administration to humans) to be effective in such treatment. A "therapeutic regimen" relates to a treatment comprising a "drug", "medication", "therapeutic", "active agent", "therapeutic compound", "composition", or "compound" as disclosed herein and/or a treatment comprising behavioral modification by the subject and/or a treatment comprising a surgical means.

As used herein, the term "encapsulation," or grammatical equivalent, refers to the process of confining an mRNA molecule within a nanoparticle. The process of incorporation of a desired mRNA into a nanoparticle is often referred to as "loading". Exemplary methods are described in Lasic, et al., FEBS Lett., 312: 255-258, 1992, which is incorporated herein by reference. The nanoparticle-incorporated nucleic acids may be completely or partially located in the interior space of the nanoparticle, within the bilayer membrane (for liposomal nanoparticles), or associated with the exterior surface of the nanoparticle.

As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein. In this application, the terms "expression" and "production," and grammatical equivalent, are used interchangeably.

As used herein, "full-length mRNA" is as characterized when using a specific assay, e.g., gel electrophoresis and detection using UV and UV absorption spectroscopy with separation by capillary electrophoresis. The length of an mRNA molecule that encodes a full-length polypeptide is at least 50% of the length of a full-length mRNA molecule that is transcribed from the target DNA, e.g., at least 60%, 70%, 80%, 90%, 91%, 92%, 93%, 94%, 95%, 96%, 97%, 98%, 99%, 99.01%, 99.05%, 99.1%, 99.2%, 99.3%, 99.4%, 99.5%, 99.6%, 99.7%, 99.8%, 99.9% of the length of a full-length mRNA molecule that is transcribed from the target DNA.

As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

As used herein, the term "impurities" refers to substances inside a confined amount of liquid, gas, or solid, which differ from the chemical composition of the target material or compound. Impurities are also referred to as contaminants.

As used herein, the term "in vitro" refers to events that occur in an artificial environment, e.g., in a test tube or reaction vessel, in cell culture, etc., rather than within a multi-cellular organism.

As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man.

As used herein, the term "messenger RNA (mRNA)" refers to a polyribonucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, in vitro transcribed, or chemically synthesized.

mRNA is typically thought of as the type of RNA that carries information from DNA to the ribosome. The existence of mRNA is usually very brief and includes processing and translation, followed by degradation. Typically, in eukaryotic organisms, mRNA processing comprises the addition of a "cap" on the N-terminal (5') end, and a "tail"

on the C-terminal (3') end. A typical cap is a 7-methyl-guanosine cap, which is a guanosine that is linked through a 5'-5'-triphosphate bond to the first transcribed nucleotide. The presence of the cap is important in providing resistance to nucleases found in most eukaryotic cells. The tail is typically a polyadenylation event whereby poly A moiety is added to the 3' end of the mRNA molecule. The presence of this "tail" serves to protect the mRNA from exonuclease degradation. Messenger RNA typically is translated by the ribosomes into a series of amino acids that make up a protein.

As used herein, the term "non-denaturing" refers to conditions that do not cause a biological material or macromolecule such as a nucleic acid or protein to lose a structure (e.g., a tertiary structure or secondary structure) that is present in its native state, by application of some external stress or compound, such as a chaotropic agent, a concentrated inorganic salt, or heat (thermal denaturing conditions). "Denaturing conditions" are conditions that cause the biological material to lose this structure. "Partially denaturing conditions" are conditions that cause the biological material to lose at least a portion of this structure.

As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA.

Furthermore, the terms "nucleic acid," "DNA," "RNA," and/or similar terms include nucleic acid analogs, i.e., analogs having other than a phosphodiester backbone As used herein, the term "shortmer" is used to specifically refer to prematurely aborted short mRNA oligonucleotide, also called short abortive RNA transcripts, which are products of incomplete mRNA transcription during in vitro transcription reactions. Shortmers, prematurely aborted mRNA, pre-abortive mRNA, or short abortive mRNA transcripts are used interchangeably in the specification.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Unless otherwise defined, all technical and scientific terms used herein have the same meaning as commonly understood by one of ordinary skill in the art to which this application belongs and as commonly used in the art to which this application belongs; such art is incorporated by reference in its entirety. In the case of conflict, the present Specification, including definitions, will control.

DETAILED DESCRIPTION OF THE INVENTION

The present invention provides large-scale in vitro synthesis methods that produce mRNA substantially free of contaminating dsRNA. The present invention provides methods of large-scale in vitro synthesis using SP6 RNA Polymerase. In some embodiments, the methods do not require a chromatography step, e.g., to remove contaminating dsRNA.

Reduction of Double-Stranded RNA (dsRNA) Contaminants

The presence of a dsRNA contaminants in in vitro synthesized mRNA is undesirable. dsRNA is immunogenic and is known to trigger a cellular response by activation of dsRNA-dependent enzymes, such as oligoadenylate synthetase (OAS), RNA-specific adenosine deaminase (ADAR), and RNA-activated protein kinase (PKR), resulting in the inhibition of protein synthesis, reducing the efficiency of mRNA therapy. The dsRNA also stimulates sensors, e.g., Toll-like receptor 3 (TLR3), retinoic acid-inducible gene I (RIG-I), and melanoma differentiation-associated protein 5 (MDA5), leading to the secretion of different cytokines, including type I interferons, interleukin-6 (IL-6), and tumor necrosis factor-α (TNF-α). Accordingly, it is desirable to eliminate or greatly reduce the amount of dsRNA from the IVT mRNA for many reasons including, for example, to limit cytokine induction.

Furthermore, dsRNA contaminants are difficult to remove from in vitro transcribed (IVT mRNA) and are oftentimes not efficiently removed from IVT mRNA during standard purification methods, including LiCl or alcohol-based precipitation, size exclusion and ion exchange chromatography, or purification based on silica matrices. Ion pair reversed-phase high-performance liquid chromatography (HPLC) is used to remove dsRNA. However, these purification method are generally not easily scalable and employ toxic reagents such as acetonitrile.

Accordingly, dsRNA generated during in vitro transcription is an undesirable by-product of mRNA synthesis. dsRNA has been shown to be highly immunogenic which creates impediments to using mRNA that contains dsRNA contaminants. To overcome this limitation, investigators have used post-synthesis purification methods in an attempt to remove dsRNA contaminants from in vitro synthesized mRNA. Potential problems associated with the post-synthesis purification methods include reduced yield and potential damage to the in vitro synthesized mRNA. The inventors of the present invention have surprisingly discovered that the use of SP6 RNA polymerase reduces or eliminates the presence of dsRNA in in vitro synthesized mRNA. Thus, the present invention can be used without the need for further post-purification steps to remove dsRNA which in turn allows for generating in vitro synthesized mRNA at high yields and with high integrity. In this manner, the post-synthesis processing for in vitro synthesized mRNA is greatly simplified.

In some embodiments, mRNA generated by in vitro transcription using SP6 RNA polymerase but not T7 RNA Polymerase was substantially free of dsRNA contaminants.

In the present invention, the methods provided do not require a purification step to remove dsRNA contaminants. In some embodiments, mRNA synthesized is used without further purification. In particular, in some embodiments, mRNA synthesized according to the present invention is used without a step of removing shortmers. In some embodiments, the mRNA product is produced without a chromatography step. In some embodiments, the mRNA product is produced without a chaotropic agent. In some embodiments, the mRNA product is produced under non-denaturing conditions. In some embodiments, the mRNA product is produced without use of lithium chloride, sodium chloride, potassium chloride, guanidium chloride, guanidium thiocyanate, guanidium isothiocyanate, ammonium acetate, and combinations thereof. In some embodiments, the entire method is performed under non-denaturing conditions.

In some embodiments, the mRNA composition is substantially free of dsRNA. In some embodiments, the mRNA composition comprises less than 0.9%, 0.8%, 0.7%, 0.6%, 0.5%, 0.4%, 0.3%, 0.2% 0.1%, 0.05%, 0.01% of the dsRNA by weight, e.g., less than 0.5%. In some embodiments, the dsRNA contaminants are reduced by greater than 99.95%, 99.9%, 99.8%, 99.7%, 99.6%, 99.5%, 99.4%, 99.3%, 99.2%, 99.1% or 99%, e.g., greater than 99.99%.

In some embodiments, the dsRNA generated by IVT using SP6 RNA polymerase is less than 10%, 8%, 5%, 4%, 3%, 2% or 1% of the dsRNA generated by IVT using T7 polymerase. In particular embodiments, the dsRNA generated by IVT using SP6 RNA polymerase is less than 1% of the dsRNA generated by IVT using T7 polymerase.

In some embodiments, the dsRNA generated by IVT using SP6 RNA polymerase is below the limit of detection. In some embodiments, the amount of dsRNA by weight is below the limit of detection in a 200 ng sample of in vitro synthesized mRNA as determined by dot blot. For example, in a typical embodiment, the amount of dsRNA by weight is below the limit of detection in a 200 ng sample of in vitro synthesized mRNA, as determined by dot blot using monoclonal antibody J2.

In some embodiments, the mRNA composition comprising native or unmodified ribonucleotides is substantially free of dsRNA. In some embodiments, the mRNA composition comprising native or unmodified ribonucleotides comprises less than 0.9%, 0.8%, 0.7%, 0.6%, 0.5%, 0.4%, 0.3%, 0.2% 0.1%, 0.05%, 0.01% of the dsRNA by weight. In some embodiments, the dsRNA is below the limit of detection in an mRNA product comprising native or unmodified ribonucleotides. In some embodiments, the amount of dsRNA by weight is below the limit of detection in a 200 ng sample of in vitro synthesized mRNA as determined by dot blot. In a typical embodiment, the amount of dsRNA by weight is below the limit of detection in a 200 ng sample of in vitro synthesized mRNA product comprising native or unmodified ribonucleotides, as determined by dot blot using monoclonal antibody J2.

In some embodiments, the mRNA composition comprising modified ribonucleotides is substantially free of dsRNA. In some embodiments, the mRNA composition comprising modified ribonucleotides comprises less than 0.9%, 0.8%, 0.7%, 0.6%, 0.5%, 0.4%, 0.3%, 0.2% 0.1%, 0.05%, 0.01% of the dsRNA by weight. In some embodiments, the dsRNA is below the limit of detection in mRNA product comprising modified ribonucleotides.

SP6 RNA Polymerase

SP6 RNA Polymerase is a DNA-dependent RNA polymerase with high sequence specificity for SP6 promoter sequences. Typically, this polymerase catalyzes the 5'→3' in vitro synthesis of RNA on either single-stranded DNA or double-stranded DNA downstream from its promoter; it incorporates native ribonucleotides and/or modified ribonucleotides into the polymerized transcript.

The sequence for bacteriophage SP6 RNA polymerase was initially described (GenBank: Y00105.1) as having the following amino acid sequence:

(SEQ ID NO: 1)
MQDLHAIQLQLEEEMFNGGIRRFEADQQRQIAAGSESDTAWNRRLLSEL

IAPMAEGIQAYKEEYEGKKGRAPRALAFLQCVENEVAAYITMKVVMDML

NTDATLQAIAMSVAERIEDQVRFSKLEGHAAKYFEKVKKSLKASRTKSY

RHAHNVAVVAEKSVAEKDADFDRWEAWPKETQLQIGTTLLEILEGSVFY

NGEPVFMRAMRTYGGKTIYYLQTSESVGQWISAFKEHVAQLSPAYAPCV

IPPRPWRTPFNGGFHTEKVASRIRLVKGNREHVRKLTQKQMPKVYKAIN

ALQNTQWQINKDVLAVIEEVIRLDLGYGVPSFKPLIDKENKPANPVPVE

FQHLRGRELKEMLSPEQWQQFINWKGECARLYTAETKRGSKSAAVVRMV

GQARKYSAFESIYFVYAMDSRSRVYVQSSTLSPQSNDLGKALLRFTEGR

PVNGVEALKWFCINGANLWGWDKKTFDVRVSNVLDEEFQDMCRDIAADP

LTFTQWAKADAPYEFLAWCFEYAQYLDLVDEGRADEFRTHLPVHQDGSC

SGIQHYSAMLRDEVGAKAVNLKPSDAPQDIYGAVAQVVIKKNALYMDAD

DATTFTSGSVTLSGTELRAMASAWDSIGITRSLTKKPVMTLPYGSTRLT

CRESVIDYIVDLEEKEAQKAVAEGRTANKVHPFEDDRQDYLTPGAAYNY

MTALIWPSISEVVKAPIVAMKMIRQLARFAAKRNEGLMYTLPTGFILEQ

KIMATEMLRVRTCLMGDIKMSLQVETDIVDEAAMMGAAAPNFVHGHDAS

HLILTVCELVDKGVTSIAVIHDSFGTHADNTLTLRVALKGQMVAMYIDG

NALQKLLEEHEVRWMVDTGIEVPEQGEFDLNEIMDSEYVFA.

An SP6 RNA polymerase suitable for the present invention can be any enzyme having substantially the same polymerase activity as bacteriophage SP6 RNA polymerase. Thus, in some embodiments, an SP6 RNA polymerase suitable for the present invention may be modified from SEQ ID NO: 1. For example, a suitable SP6 RNA polymerase may contain one or more amino acid substitutions, deletions, or additions. In some embodiments, a suitable SP6 RNA polymerase has an amino acid sequence about 99%, 98%, 97%, 96%, 95%, 94%9, 93%, 92%, 91%, 90%, 89%, 88%, 87%, 86%, 85%, 84%, 83%, 82%, 81%, 80%, 75%, 70%, 65%, or 60% identical or homologous to SEQ ID NO: 1. In some embodiments, a suitable SP6 RNA polymerase may be a truncated protein (from N-terminus, C-terminus, or internally) but retain the polymerase activity. In some embodiments, a suitable SP6 RNA polymerase is a fusion protein.

In some embodiments, an SP6 RNA Polymerase is encoded by a gene having the following nucleotide sequence:

(SEQ ID NO: 2)
ATGCAAGATTTACACGCTATCCAGCTTCAATTAGAAGAAGAGATGTTTAATGGTGGC

ATTCGTCGCTTCGAAGCAGATCAACAACGCCAGATTGCAGCAGGTAGCGAGAGCGA

CACAGCATGGAACCGCCGCCTGTTGTCAGAACTTATTGCACCTATGGCTGAAGGCAT

TCAGGCTTATAAAGAAGAGTACGAAGGTAAGAAAGGTCGTGCACCTCGCGCATTGG

CTTTCTTACAATGTGTAGAAAATGAAGTTGCAGCATACATCACTATGAAAGTTGTTA

-continued

```
TGGATATGCTGAATACGGATGCTACCCTTCAGGCTATTGCAATGAGTGTAGCAGAAC

GCATTGAAGACCAAGTGCGCTTTTCTAAGCTAGAAGGTCACGCCGCTAAATACTTTG

AGAAGGTTAAGAAGTCACTCAAGGCTAGCCGTACTAAGTCATATCGTCACGCTCATA

ACGTAGCTGTAGTTGCTGAAAAATCAGTTGCAGAAAAGGACGCGGACTTTGACCGT

TGGGAGGCGTGGCCAAAAGAAACTCAATTGCAGATTGGTACTACCTTGCTTGAAATC

TTAGAAGGTAGCGTTTTCTATAATGGTGAACCTGTATTTATGCGTGCTATGCGCACTT

ATGGCGGAAAGACTATTTACTACTTACAAACTTCTGAAAGTGTAGGCCAGTGGATTA

GCGCATTCAAAGAGCACGTAGCGCAATTAAGCCCAGCTTATGCCCCTTGCGTAATCC

CTCCTCGTCCTTGGAGAACTCCATTTAATGGAGGGTTCCATACTGAGAAGGTAGCTA

GCCGTATCCGTCTTGTAAAAGGTAACCGTGAGCATGTACGCAAGTTGACTCAAAAGC

AAATGCCAAAGGTTTATAAGGCTATCAACGCATTACAAAATACACAATGGCAAATC

AACAAGGATGTATTAGCAGTTATTGAAGAAGTAATCCGCTTAGACCTTGGTTATGGT

GTACCTTCCTTCAAGCCACTGATTGACAAGGAGAACAAGCCAGCTAACCCGGTACCT

GTTGAATTCCAACACCTGCGCGGTCGTGAACTGAAAGAGATGCTATCACCTGAGCA

GTGGCAACAATTCATTAACTGGAAAGGCGAATGCGCGCGCCTATATACCGCAGAAA

CTAAGCGCGGTTCAAAGTCCGCCGCCGTTGTTCGCATGGTAGGACAGGCCCGTAAAT

ATAGCGCCTTTGAATCCATTTACTTCGTGTACGCAATGGATAGCCGCAGCCGTGTCT

ATGTGCAATCTAGCACGCTCTCTCCGCAGTCTAACGACTTAGGTAAGGCATTACTCC

GCTTTACCGAGGGACGCCCTGTGAATGGCGTAGAAGCGCTTAAATGGTTCTGCATCA

ATGGTGCTAACCTTTGGGGATGGGACAAGAAAACTTTTGATGTGCGCGTGTCTAACG

TATTAGATGAGGAATTCCAAGATATGTGTCGAGACATCGCCGCAGACCCTCTCACAT

TCACCCAATGGGCTAAAGCTGATGCACCTTATGAATTCCTCGCTTGGTGCTTTGAGT

ATGCTCAATACCTTGATTTGGTGGATGAAGGAAGGGCCGACGAATTCCGCACTCACC

TACCAGTACATCAGGACGGGTCTTGTTCAGGCATTCAGCACTATAGTGCTATGCTTC

GCGACGAAGTAGGGGCCAAAGCTGTTAACCTGAAACCCTCCGATGCACCGCAGGAT

ATCTATGGGGCGGTGGCGCAAGTGGTTATCAAGAAGAATGCGCTATATATGGATGC

GGACGATGCAACCACGTTTACTTCTGGTAGCGTCACGCTGTCCGGTACAGAACTGCG

AGCAATGGCTAGCGCATGGGATAGTATTGGTATTACCCGTAGCTTAACCAAAAAGC

CCGTGATGACCTTGCCATATGGTTCTACTCGCTTAACTTGCCGTGAATCTGTGATTGA

TTACATCGTAGACTTAGAGGAAAAAGAGGCGCAGAAGGCAGTAGCAGAAGGGCGG

ACGGCAAACAAGGTACATCCTTTTGAAGACGATCGTCAAGATTACTTGACTCCGGGC

GCAGCTTACAACTACATGACGGCACTAATCTGGCCTTCTATTTCTGAAGTAGTTAAG

GCACCGATAGTAGCTATGAAGATGATACGCCAGCTTGCACGCTTTGCAGCGAAACG

TAATGAAGGCCTGATGTACACCCTGCCTACTGGCTTCATCTTAGAACAGAAGATCAT

GGCAACCGAGATGCTACGCGTGCGTACCTGTCTGATGGGTGATATCAAGATGTCCCT

TCAGGTTGAAACGGATATCGTAGATGAAGCCGCTATGATGGGAGCAGCAGCACCTA

ATTTCGTACACGGTCATGACGCAAGTCACCTTATCCTTACCGTATGTGAATTGGTAG

ACAAGGGCGTAACTAGTATCGCTGTAATCCACGACTCTTTTGGTACTCATGCAGACA

ACACCCTCACTCTTAGAGTGGCACTTAAAGGGCAGATGGTTGCAATGTATATTGATG
```

-continued

```
GTAATGCGCTTCAGAAACTACTGGAGGAGCATGAAGTGCGCTGGATGGTTGATACA

GGTATCGAAGTACCTGAGCAAGGGGAGTTCGACCTTAACGAAATCATGGATTCTGA

ATACGTATTTGCCTAA.
```

A suitable gene encoding the SP6 RNA polymerase suitable in the present may be about 99%, 98%, 97%, 96%, 95%, 94%, 93%, 92%, 91%, 90%, 89%, 88%, 87%, 86%, 85%, 84%, 83%, 82%, 81%, or 80% identical or homologous to SEQ ID NO: 2.

An SP6 RNA polymerase suitable for the invention may be a commercially-available product, e.g., from Ambion, New England Biolabs (NEB), Promega, and Roche. The SP6 may be ordered and/or custom designed from a commercial source or a non-commercial source according to the amino acid sequence of SEQ ID NO: 1 or a variant of SEQ ID NO: 1 as described herein. The SP6 may be a standard-fidelity polymerase or may be a high-fidelity/high-efficiency/high-capacity which has been modified to promote RNA polymerase activities, e.g., mutations in the SP6 RNA polymerase gene or post-translational modifications of the SP6 RNA polymerase itself. Examples of such modified SP6 include SP6 RNA Polymerase-Plus™ from Ambion, HiScribe SP6 from NEB, and RiboMAX™ and Riboprobe® Systems from Promega.

In some embodiments, a suitable SP6 RNA polymerase is a fusion protein. For example, an SP6 RNA polymerase may include one or more tags to promote isolation, purification, or solubility of the enzyme. A suitable tag may be located at the N-terminus, C-terminus, and/or internally. Non-limiting examples of a suitable tag include Calmodulin-binding protein (CBP); *Fasciola hepatica* 8-kDa antigen (Fh8); FLAG tag peptide; glutathione-S-transferase (GST); Histidine tag (e.g., hexahistidine tag (His6)); maltose-binding protein (MBP); N-utilization substance (NusA); small ubiquitin related modifier (SUMO) fusion tag; Streptavidin binding peptide (STREP); Tandem affinity purification (TAP); and thioredoxin (TrxA). Other tags may be used in the present invention. These and other fusion tags have been described, e.g., Costa et al. Frontiers in Microbiology 5 (2014): 63 and in PCT/US16/57044, the contents of which are incorporated herein by reference in their entireties. In some embodiments, a His tag is located at SP6's N-terminus.

SP6 Promoter

Any promoter that can be recognized by an SP6 RNA polymerase may be used in the present invention. Typically, an SP6 promoter comprises 5' ATTTAGGTGACACTATAG-3' (SEQ ID NO: 3). Variants of the SP6 promoter have been discovered and/or created to optimize recognition and/or binding of SP6 to its promoter. Non-limiting variants include but are not limited to:

```
                                        (SEQ ID NO: 4)
    5'-ATTTAGGGGACACTATAGAAGAG-3';

(SEQ ID NO: 5)
    5'-ATTTAGGGGACACTATAGAAGG-3';

(SEQ ID NO: 6)
    5'-ATTTAGGGGACACTATAGAAGGG-3';

(SEQ ID NO: 7)
    5'-ATTTAGGTGACACTATAGAA-3';
```

```
    -continued
                                        (SEQ ID NO: 8)
    5'-ATTTAGGTGACACTATAGAAGA-3';

(SEQ ID NO: 9)
    5'-ATTTAGGTGACACTATAGAAGAG-3';

(SEQ ID NO: 10)
    5'-ATTTAGGTGACACTATAGAAGG-3';

(SEQ ID NO: 11)
    5'-ATTTAGGTGACACTATAGAAGGG-3';

(SEQ ID NO: 12)
    5'-ATTTAGGTGACACTATAGAAGNG-3'; and (SEQ ID NO: 13)
    5'-CATACGATTTAGGTGACACTATAG-3'.
```

In addition, a suitable SP6 promoter for the present invention may be about 95%, 90%, 85%, 80%, 75%, or 70% identical or homologous to any one of SEQ ID NO: 3 to SEQ ID NO: 13. Moreover, an SP6 promoter suitable in the present invention may include one or more additional nucleotides 5' and/or 3' to any of the promoter sequences described herein.

Large-Scale mRNA Synthesis Using SP6 Polymerase

In some embodiments, the present invention relates to large-scale production of mRNA. In some embodiments, a method according to the invention synthesizes mRNA at least 100 mg, 150 mg, 200 mg, 300 mg, 400 mg, 500 mg, 600 mg, 700 mg, 800 mg, 900 mg, 1 g, 5 g, 10 g, 25 g, 50 g, 75 g, 100 g, 250 g, 500 g, 750 g, 1 kg, 5 kg, 10 kg, 50 kg, 100 kg, 1000 kg, or more at a single batch. In atypical embodiment, 1 g to 100 kg of mRNA (e.g., 100 g to 10 kg, or 250 g to 5 kg) is synthesized in a single batch. In some embodiments, 10 kg mRNA or more is synthesized in a single batch. In particular embodiments, between 10 kg and 100 kg of mRNA is synthesized in a single batch.

As used herein, the term "batch" refers to a quantity or amount of mRNA synthesized at one time, e.g., produced according to a single manufacturing setting. A batch may refer to an amount of mRNA synthesized in one reaction that occurs via a single aliquot of enzyme and/or a single aliquot of DNA template for continuous synthesis under one set of conditions. mRNA synthesized at a single batch would not include mRNA synthesized at different times that are combined to achieve the desired amount. Generally, a reaction mixture includes SP6 RNA polymerase, a linear DNA template, and an RNA polymerase reaction buffer (which may include ribonucleotides or may require addition of ribonucleotides).

In some embodiments of the present invention, 1-100 mg of SP6 RNA polymerase is used per gram (g) of mRNA produced. In some embodiments, about 1-90 mg, 1-80 mg, 1-60 mg, 1-50 mg, 1-40 mg, 10-100 mg, 10-80 mg, 10-60 mg, 10-50 mg of SP6 RNA polymerase is used per gram of mRNA produced. In some embodiments, about 5-20 mg of SP6 RNA polymerase is used to produce about 1 gram of mRNA. In some embodiments, about 0.5 to 2 grams of SP6 RNA polymerase is used to produce about 100 grams of mRNA. In some embodiments, about 5 to 20 grams of SP6 RNA polymerase is used to about 1 kilogram of mRNA. In some embodiments, at least 5 mg of SP6 RNA polymerase is used to produce at least 1 gram of mRNA. In some embodiments, at least 500 mg of SP6 RNA polymerase is used to produce at least 100 grams of mRNA. In some embodiments, at least 5 grams of SP6 RNA polymerase is used to produce at least 1 kilogram of mRNA. In some embodiments, about 10 mg, 20 mg, 30 mg, 40 mg, 50 mg, 60 mg, 70 mg, 80 mg, 90 mg, or 100 mg of plasmid DNA is used per gram of mRNA produced. In some embodiments, about 10-30 mg of plasmid DNA is used to produce about 1 gram of mRNA. In some embodiments, about 1 to 3 grams of plasmid DNA is used to produce about 100 grams of mRNA. In some embodiments, about 10 to 30 grams of plasmid DNA is used to about 1 kilogram of mRNA. In some embodiments, at least 10 mg of plasmid DNA is used to produce at least 1 gram of mRNA. In some embodiments, at least 1 gram of plasmid DNA is used to produce at least 100 grams of mRNA. In some embodiments, at least 10 grams of plasmid DNA is used to produce at least 1 kilogram of mRNA.

In some embodiments, the concentration of the SP6 RNA polymerase in the reaction mixture may be from about 1 to 100 nM, 1 to 90 nM, 1 to 80 nM, 1 to 70 nM, 1 to 60 nM, 1 to 50 nM, 1 to 40 nM, 1 to 30 nM, 1 to 20 nM, or about 1 to 10 nM. In certain embodiments, the concentration of the SP6 RNA polymerase is from about 10 to 50 nM, 20 to 50 nM, or 30 to 50 nM. A concentration of 100 to 10000 Units/mL of the SP6 RNA polymerase may be used, as examples, concentrations of 100 to 9000 Units/mL, 100 to 8000 Units/mL, 100 to 7000 Units/mL, 100 to 6000 Units/mL, 100 to 5000 Units/mL, 100 to 1000 Units/mL, 200 to 2000 Units/mL, 500 to 1000 Units/mL, 500 to 2000 Units/mL, 500 to 3000 Units/mL, 500 to 4000 Units/mL, 500 to 5000 Units/mL, 500 to 6000 Units/mL, 1000 to 7500 Units/mL, and 2500 to 5000 Units/mL may be used.

During the scaling up of the in vitro synthesis reaction mixture, the inventors of the present invention have surprisingly discovered that a similar or improved yield can be achieved by keeping the amount of the (expensive) template DNA the same while increasing the amount of (cheap) SP6 polymerase. Accordingly, in some embodiments, the concentration of SP6 RNA polymerase is adjusted while the amount of template DNA is maintained constant. For example, in some embodiments, the amount of SP6 RNA polymerase is increased while the amount of DNA template is maintained constant. In some embodiments, SP6 RNA polymerase in a reaction mixture is between about 5 mg to about 40 mg per gram target RNA, while the template DNA concentration is maintained constant. For example, in some embodiments, about 5 mg of SP6 RNA polymerase per gram target RNA is in the reaction mixture while the amount of DNA template is maintained constant. In some embodiments, about 10 mg of SP6 RNA polymerase per gram target RNA is in the reaction mixture while the DNA template is maintained constant. In some embodiments, about 15 mg of SP6 RNA polymerase per gram target RNA is in the reaction mixture while the DNA template is maintained constant. In some embodiments, about 20 mg of SP6 RNA polymerase per gram target RNA is in the reaction mixture while the DNA template is maintained constant. In some embodiments, about 25 mg of SP6 RNA polymerase per gram target RNA is in the reaction mixture while the DNA template is maintained constant. In some embodiments, about 30 mg of SP6 RNA polymerase per gram target RNA is in the reaction mixture while the DNA template is maintained constant. In some embodiments, about 35 mg of SP6 RNA polymerase per gram target RNA is in the reaction mixture while the DNA template is maintained constant. In some embodiments, about 40 mg of SP6 RNA polymerase per gram target RNA is in the reaction mixture while the DNA template is maintained constant.

In some embodiments, the invention provides a method of large-scale production of mRNA by in vitro synthesis, wherein the amount of SP6 RNA polymerase by weight in an in vitro synthesis reaction mixture is equal to or greater than the amount of DNA template by weight. For example, in some embodiments, the weight ratio of DNA template to SP6 RNA polymerase is between 1:1 and 1:3. In particular embodiments, the weight ratio of DNA template to SP6 RNA polymerase is between 1:1.5 and 1:2.5. In a specific embodiment, the weight ratio of DNA template to SP6 RNA polymerase is about 1:2. For instance, 10 mg of DNA template can yield 1 g of in vitro synthesized mRNA with 20 mg of SP6 RNA polymerase.

The concentration of each ribonucleotide (e.g., ATP, UTP, GTP, and CTP) in a reaction mixture is between about 0.1 mM and about 10 mM, e.g., between about 1 mM and about 10 mM, between about 2 mM and about 10 mM, between about 3 mM and about 10 mM, between about 1 mM and about 8 mM, between about 1 mM and about 6 mM, between about 3 mM and about 10 mM, between about 3 mM and about 8 mM, between about 3 mM and about 6 mM, between about 4 mM and about 5 mM. In some embodiments, each ribonucleotide is at about 5 mM in a reaction mixture. In some embodiments, the total concentration of rNTPs (for example, ATP, GTP, CTP and UTPs combined) used in the reaction range between 1 mM and 40 mM. In some embodiments, the total concentration of rNTPs (for example, ATP, GTP, CTP and UTPs combined) used in the reaction range between 1 mM and 30 mM, or between 1 mM and 28 mM, or between 1 mM to 25 mM, or between 1 mM and 20 mM. In some embodiments, the total rNTPs concentration is less than 30 mM. In some embodiments, the total rNTPs concentration is less than 25 mM. In some embodiments, the total rNTPs concentration is less than 20 mM. In some embodiments, the total rNTPs concentration is less than 15 mM. In some embodiments, the total rNTPs concentration is less than 10 mM.

The RNA polymerase reaction buffer typically includes a salt/buffering agent, e.g., Tris, HEPES, ammonium sulfate, sodium bicarbonate, sodium citrate, sodium acetate, potassium phosphate sodium phosphate, sodium chloride, and magnesium chloride.

The pH of the reaction mixture may be between about 6 to 8.5, from 6.5 to 8.0, from 7.0 to 7.5, and in some embodiments, the pH is 7.5.

Linear or linearized DNA template (e.g., as described above and in an amount/concentration sufficient to provide a desired amount of RNA), the RNA polymerase reaction buffer, and SP6 RNA polymerase are combined to form the reaction mixture. The reaction mixture is incubated at between about 37° C. and about 42° C. for thirty minutes to six hours, e.g., about sixty to about ninety minutes.

In some embodiments, about 5 mM NTPs, about 0.05 mg/mL SP6 RNA polymerase, and about 0.1 mg/mL DNA template in a suitable RNA polymerase reaction buffer (final reaction mixture pH of about 7.5) is incubated at about 37° C. to about 42° C. for sixty to ninety minutes.

In some embodiments, a reaction mixture contains linearized double stranded DNA template with an SP6 polymerase-specific promoter, SP6 RNA polymerase, RNase inhibitor, pyrophosphatase, 29 mM NTPs, 10 mM DTT and a reaction buffer (when at 10× is 800 mM HEPES, 20 mM spermidine, 250 mM $MgCl_2$, pH 7.7) and quantity sufficient (QS) to a desired reaction volume with RNase-free water; this reaction mixture is then incubated at 37° C. for 60 minutes. The polymerase reaction is then quenched by addition of DNase I and a DNase I buffer (when at 10× is 100 mM Tris-HCl, 5 mM MgCl$_2$ and 25 mM CaCl$_2$), pH 7.6) to facilitate digestion of the double-stranded DNA template in preparation for purification. This embodiment has been shown to be sufficient to produce 100 grams of mRNA.

In some embodiments, a reaction mixture includes NTPs at a concentration ranging from 1-10 mM, DNA template at a concentration ranging from 0.01-0.5 mg/mL, and SP6 RNA polymerase at a concentration ranging from 0.01-0.1 mg/mL, e.g., the reaction mixture comprises NTPs at a concentration of 5 mM, the DNA template at a concentration of 0.1 mg/ml, and the SP6 RNA polymerase at a concentration of 0.05 mg/mL.

DNA Template

Various nucleic acid templates may be used in the present invention. Typically, DNA templates which are either entirely double-stranded or mostly single-stranded with a double-stranded SP6 promoter sequence can be used.

Linearized plasmid DNA (linearized via one or more restriction enzymes), linearized genomic DNA fragments (via restriction enzyme and/or physical means), PCR products, and/or synthetic DNA oligonucleotides can be used as templates for in vitro transcription with SP6, provided that they contain a double-stranded SP6 promoter upstream (and in the correct orientation) of the DNA sequence to be transcribed.

In some embodiments, the linearized DNA template has a blunt-end.

In some embodiments, the DNA sequence to be transcribed may be optimized to facilitate more efficient transcription and/or translation. For example, the DNA sequence may be optimized regarding cis-regulatory elements (e.g., TATA box, termination signals, and protein binding sites), artificial recombination sites, chi sites, CpG dinucleotide content, negative CpG islands, GC content, polymerase slippage sites, and/or other elements relevant to transcription; the DNA sequence may be optimized regarding cryptic splice sites, mRNA secondary structure, stable free energy of mRNA, repetitive sequences, RNA instability motif, and/or other elements relevant to mRNA processing and stability; the DNA sequence may be optimized regarding codon usage bias, codon adaptability, internal chi sites, ribosomal binding sites (e.g., IRES), premature polyA sites, Shine-Dalgamo (SD) sequences, and/or other elements relevant to translation; and/or the DNA sequence may be optimized regarding codon context, codon-anticodon interaction, translational pause sites, and/or other elements relevant to protein folding. Optimization methods known in the art may be used in the present invention, e.g., GeneOptimizer by ThermoFisher and OptimumGene™, which is described in US 20110081708, the contents of which are incorporated herein by reference in its entirety.

In some embodiments, the DNA template includes a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, and citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

Nucleotides

Various naturally-occurring or modified nucleosides may be used to produce mRNA according to the present invention. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, pseudouridine, (e.g., N-1-methyl-pseudouridine), 2-thiouridine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

In some embodiments, the mRNA comprises one or more nonstandard nucleotide residues (referred to as "modified mRNA"). The nonstandard nucleotide residues may include, e.g., 5-methyl-cytidine ("5mC"), pseudouridine ("yU") and more specifically, 1-N-methyl-pseudouridine, and/or 2-thio-uridine ("2sU"). See, e.g., U.S. Pat. No. 8,278,036 or WO2011012316 for a discussion of such residues and their incorporation into mRNA. The mRNA may be RNA, which is defined as RNA in which 25% of U residues are 2-thio-uridine and 25% of C residues are 5-methylcytidine. Teachings for the use of RNA are disclosed US Patent Publication US20120195936 and international publication WO2011012316, both of which are hereby incorporated by reference in their entirety. The presence of nonstandard nucleotide residues may render an mRNA more stable and/or less immunogenic than a control mRNA with the same sequence but containing only standard residues. In further embodiments, the mRNA may comprise one or more nonstandard nucleotide residues chosen from isocytosine, pseudoisocytosine, 5-bromouracil, 5-propynyluracil, 6-aminopurine, 2-aminopurine, inosine, diaminopurine and 2-chloro-6-aminopurine cytosine, as well as combinations of these modifications and other nucleobase modifications. Some embodiments may further include additional modifications to the furanose ring or nucleobase. Additional modifications may include, for example, sugar modifications or substitutions (e.g., one or more of a 2'-O-alkyl modification, a locked nucleic acid (LNA)). In some embodiments, the RNAs may be complexed or hybridized with additional polynucleotides and/or peptide polynucleotides (PNA). In some embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification. In some embodiments, any of these modifications may be present in 0-100% of the nucleo-tides—for example, more than 0%, 1%, 10%, 25%, 50%, 75%, 85%, 90%, 95%, or 100% of the constituent nucleo-tides individually or in combination.

Synthesized mRNA

The present invention provides high quality in vitro synthesized mRNA. For example, the present invention provides uniformity/homogeneity of synthesized mRNA. In particular, a composition of the present invention includes a plurality of mRNA molecules which are substantially full-length. For example, at least 81%, 82%, 83%, 84%, 85%, 86%, 87%, 88%, 89%, 90%, 91%, 92%, 93%, 94%, 95%, 96%, 97%, 98%, 99%, of the mRNA molecules are full-length mRNA molecules. Such a composition is said to be "enriched" for full-length mRNA molecules. In some embodiments, mRNA synthesized according to the present invention is substantially full-length. A composition of the present invention has a greater percentage of full-length mRNA molecules than a composition that is not enriched for full-length mRNA molecules.

In the present invention, a composition or a batch is prepared without a step of specifically removing mRNA molecules that are not full-length mRNA molecules (i.e., abortive or aborted transcripts). In some embodiments, post-synthesis purification methods, such as chromatogra-phy methods (e.g., reversed phase-high performance (high pressure) liquid chromatography (RP-HPLC); size exclusion chromatography (SEC) and the like) are not used.

In some embodiments, the mRNA molecules synthesized by the present invention are greater than 500, 600, 700, 800, 900, 1000, 2000, 3000, 4000, 5000, 10,000, or more nucleo-tides in length; also included in the present invention is mRNA having any length in between.

Post-Synthesis Processing

Typically, a 5' cap and/or a 3' tail may be added after the synthesis. The presence of the cap is important in providing resistance to nucleases found in most eukaryotic cells. The presence of a "tail" serves to protect the mRNA from exonuclease degradation.

A 5' cap is typically added as follows: first, an RNA terminal phosphatase removes one of the terminal phosphate groups from the 5' nucleotide, leaving two terminal phos-phates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A, G(5')ppp(5')A and G(5')ppp(5')G. Additional cap structures are described in published US Application No. US 2016/0032356 and U.S. Provisional Application 62/464,327, filed Feb. 27, 2017, which are incorporated herein by reference.

Typically, a tail structure includes a poly(A) and/or poly (C) tail. A poly-A or poly-C tail on the 3' terminus of mRNA typically includes at least 50 adenosine or cytosine nucleo-tides, at least 150 adenosine or cytosine nucleotides, at least 200 adenosine or cytosine nucleotides, at least 250 adenos-ine or cytosine nucleotides, at least 300 adenosine or cyto-sine nucleotides, at least 350 adenosine or cytosine nucleo-tides, at least 400 adenosine or cytosine nucleotides, at least 450 adenosine or cytosine nucleotides, at least 500 adenos-ine or cytosine nucleotides, at least 550 adenosine or cytosine nucleotides, at least 600 adenosine or cytosine nucleo-tides, at least 650 adenosine or cytosine nucleotides, at least 700 adenosine or cytosine nucleotides, at least 750 adenos-ine or cytosine nucleotides, at least 800 adenosine or cyto-sine nucleotides, at least 850 adenosine or cytosine nucleo-tides, at least 900 adenosine or cytosine nucleotides, at least 950 adenosine or cytosine nucleotides, or at least 1 kb adenosine or cytosine nucleotides, respectively. In some embodiments, a poly-A or poly-C tail may be about 10 to 800 adenosine or cytosine nucleotides (e.g., about 10 to 200 adenosine or cytosine nucleotides, about 10 to 300 adenos-ine or cytosine nucleotides, about 10 to 400 adenosine or cytosine nucleotides, about 10 to 500 adenosine or cytosine nucleotides, about 10 to 550 adenosine or cytosine nucleo-tides, about 10 to 600 adenosine or cytosine nucleotides, about 50 to 600 adenosine or cytosine nucleotides, about 100 to 600 adenosine or cytosine nucleotides, about 150 to 600 adenosine or cytosine nucleotides, about 200 to 600 adenos-ine or cytosine nucleotides, about 250 to 600 adenosine or cytosine nucleotides, about 300 to 600 adenosine or cytosine nucleotides, about 350 to 600 adenosine or cytosine nucleo-tides, about 400 to 600 adenosine or cytosine nucleotides, about 450 to 600 adenosine or cytosine nucleotides, about 500 to 600 adenosine or cytosine nucleotides, about 10 to 150 adenosine or cytosine nucleotides, about 10 to 100 adenosine or cytosine nucleotides, about 20 to 70 adenosine or cytosine nucleotides, or about 20 to 60 adenosine or cytosine nucleotides) respectively. In some embodiments, a tail structure includes is a combination of poly(A) and poly(C) tails with various lengths described herein. In some embodiments, a tail structure includes at least 50%, 55%, 65%, 70%, 75%, 80%, 85%, 90%, 92%, 94%, 95%, 96%, 97%, 98%, or 99% adenosine nucleotides. In some embodi-ments, a tail structure includes at least 50%, 55%, 65%, 70%, 75%, 80%, 85%, 90%, 92%, 94%, 95%, 96%, 97%, 98%, or 99% cytosine nucleotides.

As described herein, the addition of the 5' cap and/or the 3' tail facilitates the detection of abortive transcripts gener-ated during in vitro synthesis because without capping and/or tailing, the size of those prematurely aborted mRNA transcripts can be too small to be detected. Thus, in some embodiments, the 5' cap and/or the 3' tail are added to the synthesized mRNA before the mRNA is tested for purity (e.g., the level of abortive transcripts present in the mRNA). In some embodiments, the 5' cap and/or the 3' tail are added to the synthesized mRNA before the mRNA is purified as described herein. In other embodiments, the 5' cap and/or the 3' tail are added to the synthesized mRNA after the mRNA is purified.

Post-Synthesis Purification

In some embodiments, the in vitro synthesized mRNA is precipitated to provide a suspension comprising the precipi-tated mRNA, such that it can be separated from contami-nants, e.g., by means of tangential flow filtration, depth filtration or centrifugation (e.g., using a filtering centrifuge). The suspension can comprise various contaminants from the in vitro synthesis reaction, for example, plasmid DNA and enzymes.

In some embodiments, precipitating the mRNA comprises adding one or more agents that promote precipitation of mRNA, for example one or more of an alcohol, an amphi-philic polymer, a buffer, a salt, and/or a surfactant. In particular embodiments, the one or more agents that pro-mote precipitation of the mRNA are (i) a salt (e.g., a chaotropic salt) and (ii) an alcohol or an amphiphilic poly-mer.

The precipitated mRNA is typically retained by or captured on a membrane or filter, while contaminants are removed. The retained precipitated mRNA is washed to remove the salt required for the precipitation step and to remove any remaining contaminants. Washing the retained precipitated mRNA typically involves one or more washing steps using a wash buffer.

In some embodiments, the wash buffer comprises an alcohol or an amphiphilic polymer. In some embodiments, the wash buffer comprises the alcohol (e.g. ethanol) at about at least 50%, 60%, 70%, 80% or 90% weight/volume concentration. In other embodiments, the wash buffer comprises an amphiphilic polymer such as a polyethylene glycol (PEG) or triethylene glycol monomethyl ether MTEG.

The washed retained precipitated mRNA is recovered from the membrane or filter by solubilizing the mRNA to provide an aqueous solution of mRNA that is substantially free of contaminants from the in vitro synthesis reaction.

Accordingly, in some embodiments, the invention provides a method of large-scale production of full-length messenger RNA (mRNA) that does not comprise a chromatographic step, said method comprising:

i) synthesizing mRNA in vitro using an SP6 RNA polymerase, wherein at least 1 g of mRNA (e.g., at least 250 g or at least 500 g) is synthesized in a single batch;

ii) precipitating the single batch of in vitro synthesized mRNA to remove contaminants deriving from the in vitro synthesis reaction;

iii) capturing the precipitated mRNA on a membrane or filter;

iv) washing the precipitated mRNA on the membrane or filter; and v) solubilizing the mRNA to provide an aqueous solution of mRNA that is substantially free of contaminants from the in vitro synthesis reaction (e.g., shortmers, enzyme reagents, and double stranded RNA (dsRNA)).

In particular embodiments, the step of synthesizing mRNA in vitro is performed with an amount of SP6 RNA polymerase by weight that is equal to or greater than the amount of DNA template by weight. For example, in a typical embodiment, the weight ratio of DNA template to SP6 RNA polymerase is between 1:1 and 1:3.

In particular embodiments, the amount of dsRNA in the mRNA is below the limit of detection, e.g., as determined by dot blot using monoclonal antibody J2. In further particular embodiments, more than 90% of the mRNA is full-length, e.g., as determined by analysis of the main peak in capillary electrophoresis. In a specific embodiment, the mRNA obtained in step v) of the above method comprises undetectable amounts of proteins or enzymes used in the in vitro synthesis reaction, e.g., as determined by silver stain.

Characterization of mRNA

Various methods are recognized in the art for characterizing in vitro synthesized mRNA. Full-length or abortive transcripts of mRNA may be detected and quantified using any methods available in the art, e.g. using blotting, capillary electrophoresis, chromatography, fluorescence, gel electrophoresis, HPLC, silver stain, spectroscopy, ultraviolet (UV), or UPLC, UV absorption spectroscopy with separation by capillary electrophoresis, or any combination thereof. In some embodiments, mRNA is first denatured by a Glyoxal dye before gel electrophoresis ("Glyoxal gel electrophoresis"). In some embodiments, synthesized mRNA is characterized before capping or tailing. In some embodiments, synthesized mRNA is characterized after capping and tailing.

In some embodiments, mRNA generated by the method disclosed herein comprises less than 10%, less than 9%, less than 8%, less than 7%, less than 6%, less than 5%, less than 4%, less than 3%, less than 2%, less than 1%, less than 0.5%, less than 0.1% impurities other than full-length mRNA. The impurities include IVT contaminants, e.g., proteins, enzymes, free nucleotides, shortmers and/or dsRNA.

In some embodiments, mRNA produced according to the invention is substantially free of shortmers or abortive transcripts. In particular, mRNA produced according to the invention contains undetectable level of shortmers or abortive transcripts by capillary electrophoresis or Glyoxal gel electrophoresis. As used herein, the term "shortmers" or "abortive transcripts" refers to any transcripts that are less than full-length. In some embodiments, "shortmers" or "abortive transcripts" are less than 100 nucleotides in length, less than 90, less than 80, less than 70, less than 60, less than 50, less than 40, less than 30, less than 20, or less than 10 nucleotides in length. In some embodiments, shortmers are detected or quantified after adding a 5'-cap, and/or a 3'-poly A tail.

Protein Expression mRNA synthesized according to the present invention results in more efficient protein translation. In some embodiments, mRNA synthesized according to the present invention using SP6 RNA Polymerase results in an increased protein expression once transfected into cells, e.g., by at least 2-fold, 3-fold, 4-fold, 5-fold, 10-fold, 20-fold, 30-fold, 40-fold, 50-fold, 100-fold, 500-fold, 1000-fold, or more, relative to the same amount of mRNA synthesized using T7 or T3 RNA Polymerase.

In some embodiments, mRNA synthesized according to the present invention results in an increased protein activity encoded by the mRNA once transfected into cells, e.g., by at least 2-fold, 3-fold, 4-fold, 5-fold, 10-fold, 20-fold, 30-fold, 40-fold, 50-fold, 100-fold, 500-fold, 1000-fold, or more, relative to the same amount of mRNA synthesized using T7 or T3 RNA Polymerase.

Any mRNA may be synthesized using the present invention. In some embodiments, an mRNA encodes one or more naturally occurring peptides. In some embodiments, an mRNA encodes one or more modified or non-natural peptides.

In some embodiments an mRNA encodes an intracellular protein. In some embodiments, an mRNA encodes a cytosolic protein. In some embodiments, an mRNA encodes a protein associated with the actin cytoskeleton. In some embodiments, an mRNA encodes a protein associated with the plasma membrane. In some specific embodiments, an mRNA encodes a transmembrane protein. In some specific embodiments an mRNA encodes an ion channel protein. In some embodiments, an mRNA encodes a perinuclear protein. In some embodiments, an mRNA encodes a nuclear protein. In some specific embodiments, an mRNA encodes a transcription factor. In some embodiments, an mRNA encodes a chaperone protein. In some embodiments, an mRNA encodes an intracellular enzyme (e.g., mRNA encoding an enzyme associated with urea cycle or lysosomal storage metabolic disorders). In some embodiments, an mRNA encodes a protein involved in cellular metabolism, DNA repair, transcription and/or translation. In some embodiments, an mRNA encodes an extracellular protein. In some embodiments, an mRNA encodes a protein associated with the extracellular matrix. In some embodiments an mRNA encodes a secreted protein. In specific embodiments, an mRNA used in the composition and methods of the invention may be used to express functional proteins or enzymes that are excreted or secreted by one or more target cells into the surrounding extracellular fluid (e.g., mRNA encoding hormones and/or neurotransmitters).

The present invention provides methods for producing a therapeutic composition enriched with full-length mRNA molecules encoding a peptide or polypeptide of interest for use in the delivery to or treatment of a subject, e.g., a human subject or a cell of a human subject or a cell that is treated and delivered to a human subject.

Accordingly, in certain embodiments the present invention provides a method for producing a therapeutic composition enriched with full-length mRNA substantially free of dsRNA that encodes a peptide or polypeptide for use in the delivery to or treatment of the lung of a subject or a lung cell. In certain embodiments the present invention provides a method for producing a therapeutic composition enriched with full-length mRNA substantially free of dsRNA that encodes for cystic fibrosis transmembrane conductance regulator (CFTR) protein. In certain embodiments the present invention provides a method for producing a therapeutic composition enriched with full-length mRNA substantially free of dsRNA that encodes for ATP-binding cassette subfamily A member 3 protein. In certain embodiments the present invention provides a method for producing a therapeutic composition enriched with full-length mRNA substantially free of dsRNA that encodes for dynein axonemal intermediate chain 1 protein. In certain embodiments the present invention provides a method for producing a therapeutic composition enriched with full-length mRNA substantially free of dsRNA that encodes for dynein axonemal heavy chain 5 (DNAH5) protein. In certain embodiments the present invention provides a method for producing a therapeutic composition enriched with full-length mRNA substantially free of dsRNA that encodes for alpha-1-antitrypsin protein. In certain embodiments the present invention provides a method for producing a therapeutic composition enriched with full-length mRNA substantially free of dsRNA that encodes for forkhead box P3 (FOXP3) protein. In certain embodiments the present invention provides a method for producing a therapeutic composition enriched with full-length mRNA substantially free of dsRNA that encodes one or more surfactant protein, e.g., one or more of surfactant A protein, surfactant B protein, surfactant C protein, and surfactant D protein.

In certain embodiments the present invention provides a method for producing a therapeutic composition enriched with full-length mRNA substantially free of dsRNA that encodes a peptide or polypeptide for use in the delivery to or treatment of the liver of a subject or a liver cell. Such peptides and polypeptides can include those associated with a urea cycle disorder, associated with a lysosomal storage disorder, with a glycogen storage disorder, associated with an amino acid metabolism disorder, associated with a lipid metabolism or fibrotic disorder, associated with methylmalonic acidemia, or associated with any other metabolic disorder for which delivery to or treatment of the liver or a liver cell with enriched full-length mRNA substantially free of dsRNA provides therapeutic benefit.

In certain embodiments the present invention provides a method for producing a therapeutic composition enriched with full-length mRNA substantially free of dsRNA that encodes for a protein associated with a urea cycle disorder. In certain embodiments the present invention provides a method for producing a therapeutic composition enriched with full-length mRNA substantially free of dsRNA that encodes for ornithine transcarbamylase (OTC) protein. In certain embodiments the present invention provides a method for producing a therapeutic composition enriched with full-length mRNA substantially free of dsRNA that encodes for arginosuccinate synthetase 1 protein. In certain embodiments the present invention provides a method for producing a therapeutic composition enriched with full-length mRNA substantially free of dsRNA that encodes for carbamoyl phosphate synthetase I protein. In certain embodiments the present invention provides a method for producing a therapeutic composition enriched with full-length mRNA substantially free of dsRNA that encodes for arginosuccinate lyase protein. In certain embodiments the present invention provides a method for producing a therapeutic composition enriched with full-length mRNA substantially free of dsRNA that encodes for arginase protein.

In certain embodiments the present invention provides a method for producing a therapeutic composition enriched with full-length mRNA substantially free of dsRNA that encodes for a protein associated with a lysosomal storage disorder. In certain embodiments the present invention provides a method for producing a therapeutic composition enriched with full-length mRNA substantially free of dsRNA that encodes for alpha galactosidase protein. In certain embodiments the present invention provides a method for producing a therapeutic composition enriched with full-length mRNA substantially free of dsRNA that encodes for glucocerebrosidase protein. In certain embodiments the present invention provides a method for producing a therapeutic composition enriched with full-length mRNA substantially free of dsRNA that encodes for iduronate-2-sulfatase protein. In certain embodiments the present invention provides a method for producing a therapeutic composition enriched with full-length mRNA substantially free of dsRNA that encodes for iduronidase protein. In certain embodiments the present invention provides a method for producing a therapeutic composition enriched with full-length mRNA substantially free of dsRNA that encodes for N-acetyl-alpha-D-glucosaminidase protein. In certain embodiments the present invention provides a method for producing a therapeutic composition enriched with full-length mRNA substantially free of dsRNA that encodes for heparan N-sulfatase protein. In certain embodiments the present invention provides a method for producing a therapeutic composition enriched with full-length mRNA substantially free of dsRNA that encodes for galactosamine-6 sulfatase protein. In certain embodiments the present invention provides a method for producing a therapeutic composition enriched with full-length mRNA substantially free of dsRNA that encodes for beta-galactosidase protein. In certain embodiments the present invention provides a method for producing a therapeutic composition enriched with full-length mRNA substantially free of dsRNA that encodes for lysosomal lipase protein. In certain embodiments the present invention provides a method for producing a therapeutic composition enriched with full-length mRNA substantially free of dsRNA that encodes for arylsulfatase B (N-acetvRalactosamine-4-sulfatase) protein. In certain embodiments the present invention provides a method for producing a therapeutic composition enriched with full-length mRNA substantially free of dsRNA that encodes for transcription factor EB (TFEB).

In certain embodiments the present invention provides a method for producing a therapeutic composition enriched with full-length mRNA substantially free of dsRNA that encodes for Firefly Luciferase enzyme (FFL). In certain embodiments the present invention provides a method for producing a therapeutic composition enriched with full-length mRNA substantially free of dsRNA that encodes for human erythropoietin (EPO) mRNA.

In certain embodiments the present invention provides a method for producing a therapeutic composition enriched with full-length mRNA substantially free of dsRNA that encodes for a protein associated with a glycogen storage disorder. In certain embodiments the present invention provides a method for producing a therapeutic composition enriched with full-length mRNA substantially free of dsRNA that encodes for acid alpha-glucosidase protein. In certain embodiments the present invention provides a method for producing a therapeutic composition enriched with full-length mRNA substantially free of dsRNA that encodes for glucose-6-phosphatase (G6PC) protein. In certain embodiments the present invention provides a method for producing a therapeutic composition enriched with full-length mRNA substantially free of dsRNA that encodes for liver glycogen phosphorylase protein. In certain embodiments the present invention provides a method for producing a therapeutic composition enriched with full-length mRNA substantially free of dsRNA that encodes for muscle phosphoglycerate mutase protein. In certain embodiments the present invention provides a method for producing a therapeutic composition enriched with full-length mRNA substantially free of dsRNA that encodes for glycogen debranching enzyme.

In certain embodiments the present invention provides a method for producing a therapeutic composition enriched with full-length mRNA substantially free of dsRNA that encodes for a protein associated with amino acid metabolism. In certain embodiments the present invention provides a method for producing a therapeutic composition enriched with full-length mRNA substantially free of dsRNA that encodes for phenylalanine hydroxylase (PAH) enzyme. In certain embodiments the present invention provides a method for producing a therapeutic composition enriched with full-length mRNA substantially free of dsRNA that encodes for glutaryl-CoA dehydrogenase enzyme. In certain embodiments the present invention provides a method for producing a therapeutic composition enriched with full-length mRNA substantially free of dsRNA that encodes for propionyl-CoA carboxylase enzyme. In certain embodiments the present invention provides a method for producing a therapeutic composition enriched with full-length mRNA substantially free of dsRNA that encodes for oxalase alanine-glyoxylate aminotransferase enzyme.

In certain embodiments the present invention provides a method for producing a therapeutic composition enriched with full-length mRNA substantially free of dsRNA that encodes for a protein associated with a lipid metabolism or fibrotic disorder. In certain embodiments the present invention provides a method for producing a therapeutic composition enriched with full-length mRNA substantially free of dsRNA that encodes for an mTOR inhibitor. In certain embodiments the present invention provides a method for producing a therapeutic composition enriched with full-length mRNA substantially free of dsRNA that encodes for ATPase phospholipid transporting 8B1 (ATP8B1) protein. In certain embodiments the present invention provides a method for producing a therapeutic composition enriched with full-length mRNA substantially free of dsRNA that encodes for one or more NF-kappa B inhibitors, such as one or more of I-kappa B alpha, interferon-related development regulator 1 (IFRD1), and Sirtuin 1 (SIRT1). In certain embodiments the present invention provides a method for producing a therapeutic composition enriched with full-length mRNA substantially free of dsRNA that encodes for PPAR-gamma protein or an active variant.

In certain embodiments the present invention provides a method for producing a therapeutic composition enriched with full-length mRNA substantially free of dsRNA that encodes for a protein associated with methylmalonic acidemia. For example, in certain embodiments the present invention provides a method for producing a therapeutic composition enriched with full-length mRNA substantially free of dsRNA that encodes for methylmalonyl CoA mutase protein. In certain embodiments the present invention provides a method for producing a therapeutic composition enriched with full-length mRNA substantially free of dsRNA that encodes for methylmalonyl CoA epimerase protein.

In certain embodiments the present invention provides a method for producing a therapeutic composition enriched with full-length mRNA substantially free of dsRNA for which delivery to or treatment of the liver can provide therapeutic benefit. In certain embodiments the present invention provides a method for producing a therapeutic composition enriched with full-length mRNA substantially free of dsRNA that encodes for ATP7B protein, also known as Wilson disease protein. In certain embodiments the present invention provides a method for producing a therapeutic composition enriched with full-length mRNA substantially free of dsRNA that encodes for porphobilinogen deaminase enzyme. In certain embodiments the present invention provides a method for producing a therapeutic composition enriched with full-length mRNA substantially free of dsRNA that encodes for one or clotting enzymes, such as Factor VIII, Factor IX, Factor VII, and Factor X. In certain embodiments the present invention provides a method for producing a therapeutic composition enriched with full-length mRNA substantially free of dsRNA that encodes for human hemochromatosis (HFE) protein.

In certain embodiments the present invention provides a method for producing a therapeutic composition enriched with full-length mRNA substantially free of dsRNA that encodes a peptide or polypeptide for use in the delivery to or treatment of the cardiovasculature of a subject or a cardiovascular cell. In certain embodiments the present invention provides a method for producing a therapeutic composition enriched with full-length mRNA substantially free of dsRNA that encodes for vascular endothelial growth factor A protein. In certain embodiments the present invention provides a method for producing a therapeutic composition enriched with full-length mRNA substantially free of dsRNA that encodes for relaxin protein. In certain embodiments the present invention provides a method for producing a therapeutic composition enriched with full-length mRNA substantially free of dsRNA that encodes for bone morphogenetic protein-9 protein. In certain embodiments the present invention provides a method for producing a therapeutic composition enriched with full-length mRNA substantially free of dsRNA that encodes for bone morphogenetic protein-2 receptor protein.

In certain embodiments the present invention provides a method for producing a therapeutic composition enriched with full-length mRNA substantially free of dsRNA that encodes a peptide or polypeptide for use in the delivery to or treatment of the muscle of a subject or a muscle cell. In certain embodiments the present invention provides a method for producing a therapeutic composition enriched with full-length mRNA substantially free of dsRNA that encodes for dystrophin protein. In certain embodiments the present invention provides a method for producing a therapeutic composition enriched with full-length mRNA substantially free of dsRNA that encodes for frataxin protein. In certain embodiments the present invention provides a method for producing a therapeutic composition enriched with full-length mRNA substantially free of dsRNA that encodes a peptide or polypeptide for use in the delivery to or treatment of the cardiac muscle of a subject or a cardiac muscle cell. In certain embodiments the present invention provides a method for producing a therapeutic composition enriched with full-length mRNA substantially free of dsRNA that encodes for a protein that modulates one or both of a potassium channel and a sodium channel in muscle tissue or in a muscle cell. In certain embodiments the present invention provides a method for producing a therapeutic composition enriched with full-length mRNA substantially free of dsRNA that encodes for a protein that modulates a Kv7.1 channel in muscle tissue or in a muscle cell. In certain embodiments the present invention provides a method for producing a therapeutic composition enriched with full-length mRNA substantially free of dsRNA that encodes for a protein that modulates a Nav1.5 channel in muscle tissue or in a muscle cell.

In certain embodiments the present invention provides a method for producing a therapeutic composition enriched with full-length mRNA substantially free of dsRNA that encodes a peptide or polypeptide for use in the delivery to or treatment of the nervous system of a subject or a nervous system cell. For example, in certain embodiments the present invention provides a method for producing a therapeutic composition enriched with full-length mRNA substantially free of dsRNA that encodes for survival motor neuron 1 protein. For example, in certain embodiments the present invention provides a method for producing a therapeutic composition enriched with full-length mRNA substantially free of dsRNA that encodes for survival motor neuron 2 protein. In certain embodiments the present invention provides a method for producing a therapeutic composition enriched with full-length mRNA substantially free of dsRNA that encodes for frataxin protein. In certain embodiments the present invention provides a method for producing a therapeutic composition enriched with full-length mRNA substantially free of dsRNA that encodes for ATP binding cassette subfamily D member 1 (ABCD1) protein. In certain embodiments the present invention provides a method for producing a therapeutic composition enriched with full-length mRNA substantially free of dsRNA that encodes for CLN3 protein.

In certain embodiments the present invention provides a method for producing a therapeutic composition enriched with full-length mRNA substantially free of dsRNA that encodes a peptide or polypeptide for use in the delivery to or treatment of the blood or bone marrow of a subject or a blood or bone marrow cell. In certain embodiments the present invention provides a method for producing a therapeutic composition enriched with full-length mRNA substantially free of dsRNA that encodes for beta globin protein. In certain embodiments the present invention provides a method for producing a therapeutic composition enriched with full-length mRNA substantially free of dsRNA that encodes for Bruton's tyrosine kinase protein. In certain embodiments the present invention provides a method for producing a therapeutic composition enriched with full-length mRNA substantially free of dsRNA that encodes for one or clotting enzymes, such as Factor VIII, Factor IX, Factor VII, and Factor X.

In certain embodiments the present invention provides a method for producing a therapeutic composition enriched with full-length mRNA substantially free of dsRNA that encodes a peptide or polypeptide for use in the delivery to or treatment of the kidney of a subject or a kidney cell. In certain embodiments the present invention provides a method for producing a therapeutic composition enriched with full-length mRNA substantially free of dsRNA that encodes for collagen type IV alpha 5 chain (COL4A5) protein.

In certain embodiments the present invention provides a method for producing a therapeutic composition enriched with full-length mRNA substantially free of dsRNA that encodes a peptide or polypeptide for use in the delivery to or treatment of the eye of a subject or an eye cell. In certain embodiments the present invention provides a method for producing a therapeutic composition enriched with full-length mRNA substantially free of dsRNA that encodes for ATP-binding cassette sub-family A member 4 (ABCA4) protein. In certain embodiments the present invention provides a method for producing a therapeutic composition enriched with full-length mRNA substantially free of dsRNA that encodes for retinoschisin protein. In certain embodiments the present invention provides a method for producing a therapeutic composition enriched with full-length mRNA substantially free of dsRNA that encodes for retinal pigment epithelium-specific 65 kDa (RPE65) protein. In certain embodiments the present invention provides a method for producing a therapeutic composition enriched with full-length mRNA substantially free of dsRNA that encodes for centrosomal protein of 290 kDa (CEP290).

In certain embodiments the present invention provides a method for producing a therapeutic composition enriched with full-length mRNA substantially free of dsRNA that encodes a peptide or polypeptide for use in the delivery of or treatment with a vaccine for a subject or a cell of a subject. For example, in certain embodiments the present invention provides a method for producing a therapeutic composition enriched with full-length mRNA substantially free of dsRNA that encodes for an antigen from an infectious agent, such as a virus. In certain embodiments the present invention provides a method for producing a therapeutic composition enriched with full-length mRNA substantially free of dsRNA that encodes for an antigen from influenza virus. In certain embodiments the present invention provides a method for producing a therapeutic composition enriched with full-length mRNA substantially free of dsRNA that encodes for an antigen from respiratory syncytial virus. In certain embodiments the present invention provides a method for producing a therapeutic composition enriched with full-length mRNA substantially free of dsRNA that encodes for an antigen from rabies virus. In certain embodiments the present invention provides a method for producing a therapeutic composition enriched with full-length mRNA substantially free of dsRNA that encodes for an antigen from cytomegalovirus. In certain embodiments the present invention provides a method for producing a therapeutic composition enriched with full-length mRNA substantially free of dsRNA that encodes for an antigen from rotavirus. In certain embodiments the present invention provides a method for producing a therapeutic composition enriched with full-length mRNA substantially free of dsRNA that encodes for an antigen from a hepatitis virus, such as hepatitis A virus, hepatitis B virus, or hepatitis C virus. In certain embodiments the present invention provides a method for producing a therapeutic composition enriched with full-length mRNA substantially free of dsRNA that encodes for an antigen from human papillomavirus. In certain embodiments the present invention provides a method for producing a therapeutic composition enriched with full-length mRNA substantially free of dsRNA that encodes for an antigen from a herpes simplex virus, such as herpes simplex virus 1 or herpes simplex virus 2. In certain embodiments the present invention provides a method for producing a therapeutic composition enriched with full-length mRNA substantially free of dsRNA that encodes for an antigen from a human immunodeficiency virus, such as human immunodeficiency virus type 1 or human immunodeficiency virus type 2. In certain embodiments the present invention provides a method for producing a therapeutic composition enriched with full-length mRNA substantially free of dsRNA that encodes for an antigen from a human metapneumovirus. In certain embodiments the present invention provides a method for producing a therapeutic composition enriched with full-length mRNA substantially free of dsRNA that encodes for an antigen from a human parainfluenza virus, such as human parainfluenza virus type 1, human parainfluenza virus type 2, or human parainfluenza virus type 3. In certain embodiments the present invention provides a method for producing a therapeutic composition enriched with full-length mRNA substantially free of dsRNA that encodes for an antigen from malaria virus. In certain embodiments the present invention provides a method for producing a therapeutic composition enriched with full-length mRNA substantially free of dsRNA that encodes for an antigen from zika virus. In certain embodiments the present invention provides a method for producing a therapeutic composition enriched with full-length mRNA substantially free of dsRNA that encodes for an antigen from chikungunya virus.

In certain embodiments the present invention provides a method for producing a therapeutic composition enriched with full-length mRNA substantially free of dsRNA that encodes for an antigen associated with a cancer of a subject or identified from a cancer cell of a subject. In certain embodiments the present invention provides a method for producing a therapeutic composition enriched with full-length mRNA substantially free of dsRNA that encodes for an antigen determined from a subject's own cancer cell, i.e., to provide a personalized cancer vaccine. In certain embodiments the present invention provides a method for producing a therapeutic composition enriched with full-length mRNA substantially free of dsRNA that encodes for an antigen expressed from a mutant KRAS gene.

In certain embodiments the present invention provides a method for producing a therapeutic composition enriched with full-length mRNA substantially free of dsRNA that encodes for an antibody. In certain embodiments, the antibody can be a bi-specific antibody. In certain embodiments, the antibody can be part of a fusion protein. In certain embodiments the present invention provides a method for producing a therapeutic composition enriched with full-length mRNA substantially free of dsRNA that encodes for an antibody to OX40. In certain embodiments the present invention provides a method for producing a therapeutic composition enriched with full-length mRNA substantially free of dsRNA that encodes for an antibody to VEGF. In certain embodiments the present invention provides a method for producing a therapeutic composition enriched with full-length mRNA substantially free of dsRNA that encodes for an antibody to tissue necrosis factor alpha. In certain embodiments the present invention provides a method for producing a therapeutic composition enriched with full-length mRNA substantially free of dsRNA that encodes for an antibody to CD3. In certain embodiments the present invention provides a method for producing a therapeutic composition enriched with full-length mRNA substantially free of dsRNA that encodes for an antibody to CD19.

In certain embodiments the present invention provides a method for producing a therapeutic composition enriched with full-length mRNA substantially free of dsRNA that encodes for an immunomodulator. In certain embodiments the present invention provides a method for producing a therapeutic composition enriched with full-length mRNA substantially free of dsRNA that encodes for Interleukin 12. In certain embodiments the present invention provides a method for producing a therapeutic composition enriched with full-length mRNA substantially free of dsRNA that encodes for Interleukin 23. In certain embodiments the present invention provides a method for producing a therapeutic composition enriched with full-length mRNA substantially free of dsRNA that encodes for Interleukin 36 gamma. In certain embodiments the present invention provides a method for producing a therapeutic composition enriched with full-length mRNA substantially free of dsRNA that encodes for a constitutively active variant of one or more stimulator of interferon genes (STING) proteins.

In certain embodiments the present invention provides a method for producing a therapeutic composition enriched with full-length mRNA substantially free of dsRNA that encodes for an endonuclease. In certain embodiments the present invention provides a method for producing a therapeutic composition enriched with full-length mRNA substantially free of dsRNA that encodes for an RNA-guided DNA endonuclease protein, such as Cas 9 protein. In certain embodiments the present invention provides a method for producing a therapeutic composition enriched with full-length mRNA substantially free of dsRNA that encodes for a meganuclease protein. In certain embodiments the present invention provides a method for producing a therapeutic composition enriched with full-length mRNA substantially free of dsRNA that encodes for a transcription activator-like effector nuclease protein. In certain embodiments the present invention provides a method for producing a therapeutic composition enriched with full-length mRNA substantially free of dsRNA that encodes for a zinc finger nuclease protein.

Lipid Nanoparticles mRNA synthesized according to the present invention may be formulated and delivered for in vivo protein production using any method. In some embodiments, mRNA is encapsulated, into a transfer vehicle, such as a nanoparticle. Among other things, one purpose of such encapsulation is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue. In some embodiments, nanoparticles may be lipid-based nanoparticles, e.g., comprising a liposome, or polymer-based nanoparticles. In some embodiments, a nanoparticle may have a diameter of less than about 40-100 nm. A nanoparticle may include at least 1 μg, 10 μg, 100 μg, 1 mg, 10 mg, 100 mg, 1 g, or more mRNA.

In some embodiments, the transfer vehicle is a liposomal vesicle, or other means to facilitate the transfer of a nucleic acid to target cells and tissues. Suitable transfer vehicles include, but are not limited to, liposomes, nanoliposomes, ceramide-containing nanoliposomes, proteoliposomes, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), nanodendrimers, starch-based delivery systems, micelles, emulsions, niosomes, plasmids, viruses, calcium phosphate nucleotides, aptamers, peptides and other vectorial tags. Also contemplated is the use of bionanocapsules and other viral capsid proteins assemblies as a suitable transfer vehicle. (Hum. Gene Ther. 2008 September; 19(9):887-95).

A liposome may include one or more cationic lipids, one or more non-cationic lipids, one or more sterol-based lipids, and/or one or more PEG-modified lipids. A liposome may include three or more distinct components of lipids, one distinct component of lipids being sterol-based cationic lipids. In some embodiments, the sterol-based cationic lipid is an imidazole cholesterol ester or "ICE" lipid (see, WO 2011/068810, which is incorporated by reference in its entirety). In some embodiments, sterol-based cationic lipids constitute no more than 70% (e.g., no more than 65% and 60%) of the total lipids in a lipid nanoparticle (e.g., liposome).

Examples of suitable lipids include, for example, the phosphatidyl compounds (e.g., phosphatidylglycerol, phosphatidylcholine, phosphatidylserine, phosphatidylethanolamine, sphingolipids, cerebrosides, and gangliosides).

Non-limiting examples of cationic lipids include C12-200, MC3, DLinDMA, DLinkC2DMA, cKK-E12, ICE (Imidazole-based), HGT5000, HGT5001, OF-02, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, and HGT4003, or a combination thereof.

Non-limiting examples of non-cationic lipids include ceramide; cephalin; cerebrosides; diacylglycerols; 1,2-dipalmitoyl-sn-glycero-3-phosphorylglycerol sodium salt (DPPG); 1,2-distearoyl-sn-glycero-3-phosphoethanolamine (DSPE); 1,2-distearoyl-sn-glycero-3-phosphocholine (DSPC); 1,2-dipalmitoyl-sn-glycero-3-phosphocholine (DPPC); 1,2-dioleyl-sn-glycero-3-phosphoethanolamine (DOPE); 1,2-dioleyl-sn-glycero-3-phosphotidylcholine (DOPC); 1,2-dipalmitoyl-sn-glycero-3-phosphoethanolamine (DPPE); 1,2-dimyristoyl-sn-glycero-3-phosphoethanolamine (DMPE); and 1,2-dioleoyl-sn-glycero-3-phospho-(1'-rac-glycerol) (DOPG), 1-palmitoyl-2-oleoyl-phosphatidylethanolamine (POPE); 1-palmitoyl-2-oleoyl-sn-glycero-3-phosphocholine (POPC); 1-stearoyl-2-oleoyl-phosphatidylethanolamine (SOPE); sphingomyelin; or a combination thereof.

In some embodiments, a PEG-modified lipid may be a poly(ethylene) glycol chain of up to 5 kDa in length covalently attached to a lipid with alkyl chain(s) of $C_6$-$C_{20}$ length. Non-limiting examples of PEG-modified lipids include DMG-PEG, DMG-PEG2K, C8-PEG, DOG PEG, ceramide PEG, and DSPE-PEG, or a combination thereof.

Also contemplated is the use of polymers as transfer vehicles, whether alone or in combination with other transfer vehicles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins and polyethylenimine. A polymer-based nanoparticles may include polyethylenimine (PEI), e.g., a branched PEI.

Additional teaching relevant to the present invention are described in one or more of the following: WO2011/068810, WO2012/075040, U.S. Ser. No. 15/294,249, U.S. 62/420, 421, and U.S. 62/421,021, and the related applications filed Feb. 27, 2017 by Applicants entitled "METHODS FOR PURIFICATION OF MESSENGER RNA", "NOVEL CODON-OPTIMIZED CFTR SEQUENCE", and "METHODS FOR PURIFICATION OF MESSENGER RNA", each of which is incorporated by reference in its entirety.

Although methods and materials similar or equivalent to those described herein can be used in the practice or testing of the present invention, suitable methods and materials are described below. All publications, patent applications, patents, and other references mentioned herein are incorporated by reference in their entirety. The references cited herein are not admitted to be prior art to the claimed invention. In addition, the materials, methods, and examples are illustrative only and are not intended to be limiting.

EXAMPLES

Example 1: In Vitro Transcription Using SP6 RNA Polymerase, not T7 RNA Polymerase, Generated mRNA Product that was Substantially Free of Double-Stranded RNA This example illustrates the amount of double-stranded RNA present in mRNA product generated by in vitro transcription (IVT) using SP6 RNA polymerase or T7 RNA polymerase as detected by a dot blot.

The process of in vitro transcription generates double-stranded RNA through base pairing in regions of complementarity within the same strand or on opposite strands yielding dsRNA with 5' or 3' overhangs (FIG. 1). The dsRNA is an undesirable contaminant for applications of mRNA therapy.

In order to measure the amounts of double-stranded RNA generated during in vitro transcription by SP6 RNA polymerase or T7 RNA polymerase, mRNA synthesis was first carried out. The T7 transcription reaction consisted of 1× T7 transcription buffer (80 mM HEPES pH 8.0, 2 mM Spermidine, and 25 mM $MgCl_2$ with a final pH of 7.7), 10 mM DTT, 7.25 mM each ATP, GTP, CTP, and UTP, RNAse Inhibitor, Pyrophosphatase, and T7 RNA Polymerase. The SP6 reaction included 5 mM of each NTP, about 0.05 mg/mL SP6 polymerase DNA, and about 0.1 mg/mL template DNA; other components of transcription buffer varied. The reactions were performed for 60 to 90 minutes (unless otherwise noted) at 37° C. DNAseI was added to stop the reaction and incubated for 15 more minutes at 37° C. The in vitro transcribed mRNA was purified using the Qiagen RNA maxi column following manufacturer's recommendations. The purified mRNA product from the aforementioned in vitro transcription step was treated with portions of GTP (1.0 mM), S-adenosyl methionine, RNAse inhibitor, 2'-O-Methyltransferase and guanylyl transferase are mixed together with reaction buffer (10×, 500 mM Tris-HCl (pH 8.0), 60 mM KCl, 12.5 mM $MgCl_2$). The combined solution was incubated for a range of time at 37° C. for 30 to 90 minutes. Upon completion, aliquots of ATP (2.0 mM), PolyA Polymerase and tailing reaction buffer (10×, 500 mM Tris-HCl (pH 8.0), 2.5 M NaCl, 100 mM $MgCl_2$) were added and the total reaction mixture was further incubated at 37° C. for a range of time from 20 to 45 minutes. Upon completion, the final reaction mixture was quenched and purified accordingly.

Briefly, for each gram of mRNA transcribed, a reaction containing 20 mg of a linearized double stranded DNA plasmid with an RNA polymerase-specific promoter, 10 mg RNA polymerase, RNase inhibitor, pyrophosphatase, 5 mM NTPs, 10 mM DTT and a reaction buffer (10×—250 mM Tris-HCl, pH 7.5, 20 mM spermidine,50 mM NaCl,) was used and quantity sufficient (QS) to 200 mL with RNase-free water then incubated at 37 C for 60 min. The reaction was then quenched by the addition of DNase I and a DNase I buffer (10×—100 mM Tris-HCl, 5 mM MgCl$_2$ and 25 mM CaCl$_2$), pH 7.6) to facilitate digestion of the double-stranded DNA template.

In some embodiments, purified in vitro transcribed mRNA was modified enzymatically by the addition of a 5' N$^7$-methylguanylate cap 0 structure using guanylate transferase and the addition of a methyl group at the 2' 0 position of the penultimate nucleotide resulting in a Cap 1 structure using 2' O-methyltransferase as described by Fechter, P.; Brownlee, G. G. "Recognition of mRNA cap structures by viral and cellular proteins" *J Gen. Virology* 2005, 86, 1239-1249. Following addition of the Cap 1 structure, a polyadenylate tail was added to the 3' end of the in vitro transcribed mRNA enzymatically using poly-A polymerase. Briefly, a capping reaction was set up for every gram of purified IVT containing 2.5 mM GTP, 246 µM S-adenosyl methionine, RNase inhibitor, 2'-Omethyl transferase, guanylyl transferase, a reaction buffer (10×—500 mM Tris-HCl pH 8.0, 60 mM MgCl$_2$, and 12.5 mM MgCl$_2$) and QS to 650 mL with RNase-free H$_2$O then incubated at 37 C for 60 minutes. Following the incubation, a tailing reaction was initiated by adding tailing buffer (10×—500 mM Tris-HCl pH 8.0, 2.5 M NaCl, 100 mM MgCl$_2$), 3.7 mM ATP, poly-A polymerase and QS to 800 mL with RNase-free H$_2$O. The tailing reaction was carried out at 37° C. for 30 minutes before the addition of 12.5 mM EDTA to quench.

A dot blot was carried out to detect the amount of double-stranded RNA generated during mRNA synthesis by SP6 RNA polymerase or T7 RNA polymerase. The dot blot was carried out on mRNA product either before or after capping and tailing the transcribed RNA. 200 ng of RNA was blotted per SAM HA sample in a 2 µL sample volume. An Anti-dsRNA monoclonal antibody J2 was used as the primary antibody while an anti-mouse IgG HRP was used as secondary antibody. The J2 antibody recognizes dsRNA provided that the length of the helix is greater than or equal to 40 bp. dsRNA-recognition is independent of the sequence and nucleotide composition of the mRNA. The J2 antibody is the gold standard for the detection of dsRNA.

Signal was detected after a one-minute exposure (FIG. 2) and compared to the signal obtained from 2 ng or 25 ng of double-stranded RNA standard loaded as controls. The results showed that greater than 25 ng of double-stranded RNA was generated using T7 RNA polymerase (FIG. 2, lanes labelled 3 and 4). In contrast, the amount of dsRNA generated in the reaction using SP6 RNA polymerase was lower than the limit of detection (FIG. 2, lanes labelled 1 and 2).

These results showed that synthesis of mRNA by IVT using SP6 RNA polymerase generated mRNA that was substantially free of double-stranded RNA, suitable for downstream applications. Using SP6 RNA polymerase is a method of generating mRNA by IVT without substantial amounts of double-stranded RNA.

Example 2: Exemplary SP6 Polymerase-Derived mRNA Products were Substantially Free of Double-Stranded RNA as Compared to Corresponding T7 Polymerase-Derived mRNA Products This example demonstrates that exemplary mRNA products synthesized by SP6 RNA polymerase were substantially free of double-stranded RNA, as compared to corresponding mRNA products synthesized by T7 polymerase.

Exemplary mRNAs including Human Cystic Fibrosis Transmembrane Conductance Regulator (CFTR) mRNA, Firefly Luciferase (FFL) mRNA, Phenylalanine Hydroxylase (PAH) mRNA, Ornithine Trans Carbamylase (OTC) mRNA, or human erythropoietin (EPO) mRNA were in vitro transcribed using SP6 RNA polymerase or using T7 polymerase respectively, based on the conditions described in Example 1.

In order to measure the amount of double-stranded RNA, a dot blot was carried out on 200 ng of mRNA transcribed using SP6 polymerase or T7 polymerase. The blot was probed with an anti-dsRNA J2 monoclonal antibody and then incubated with secondary anti-mouse IgG horse radish peroxidase antibody. The signal obtained with each of the samples was compared to a control 25 ng dsRNA marker (FIG. 3, lane 1).

The results showed that mRNA generated using T7 polymerase contained detectable CFTR double-stranded RNA up to about 25 ng out of 200 ng of RNA blotted (i.e. 12.5%). In contrast, mRNA synthesized using SP6 RNA polymerase contained less than 25 ng detectable double-stranded CFTR RNA (FIG. 3, lane 2).

Figure 3:
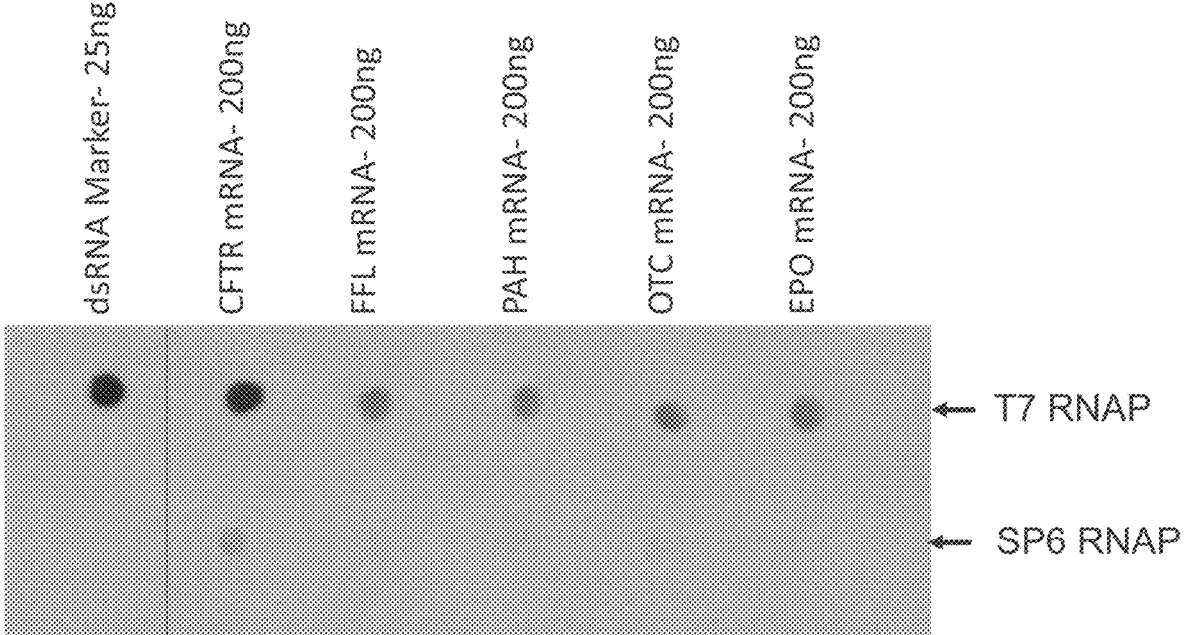
FIG. 3 is a dot blot showing a comparison of the amount of dsRNA present in exemplary mRNA products generated by in vitro transcription using SP6 RNA Polymerase versus T7 polymerase. Exemplary mRNA products included Human Cystic Fibrosis Transmembrane Conductance Regulator (CFTR) mRNA (lane 2), Firefly Luciferase (FFL) mRNA (lane 3), Phenylalanine Hydroxylase (PAH) mRNA (lane 4), Ornithine Trans Carbamylase (OTC) mRNA (lane 5), or human erythropoietin (EPO) mRNA (lane 6) relative to a dsRNA control (lane 1).

Similarly, while T7 polymerase transcribed FFL, PAH, OTC and EPO mRNA products contained less than 25 ng of double-stranded RNA, the amount of double-stranded RNA in SP6 RNA polymerase transcribed FFL, PAH, OTC and EPO mRNA products was below the limit of detection (FIG. 3, lanes 3-6).

These results showed that synthesis of mRNA by IVT using SP6 RNA polymerase generated various exemplary mRNA products that were substantially free of dsRNA, suitable for downstream applications. Using SP6 polymerase is a widely applicable method of generating mRNA products by IVT without substantial amounts of dsRNA.

Example 3: Scaling Up to Milligram Quantities of mRNA Using SP6 Polymerase Generated mRNA Product that was Substantially Free of Double-Stranded RNA This example illustrates the amount of double-stranded RNA generated by large-scale in vitro transcription yielding milligram quantities of mRNA product. Exemplary mRNAs were synthesized using SP6 RNA polymerase and T7 RNA polymerase respectively, based on the conditions described in Example 1. The procedure was scaled up to generate milligram quantities of mRNA in a single batch.

Exemplary mRNAs including Human Cystic Fibrosis Transmembrane Conductance Regulator (CFTR) mRNA, Phenylalanine Hydroxylase (PAH) mRNA, Ornithine Trans Carbamylase (OTC) mRNA, or HA mRNA were transcribed using T7 RNA polymerase (Old Process) or SP6 RNA polymerase (New Process).

In order to measure the amount of double-stranded RNA, a dot blot was carried out on milligram quantities of mRNA transcribed using T7 RNA polymerase (Old Process) or SP6 RNA Polymerase (New Process). The blot was probed with an anti-dsRNA J2 monoclonal antibody and then incubated with secondary anti-mouse IgG horse radish peroxidase antibody. Signal detected from each of the samples after a one-minute exposure was compared to the signal obtained from a dsRNA control.

Figure 4A:
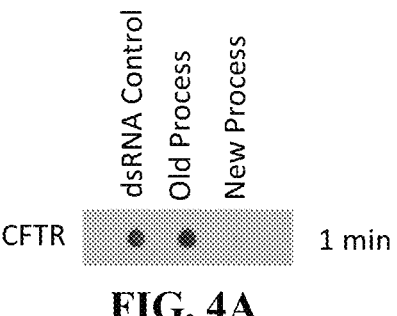
FIG. 4A is a dot blot showing a comparison of the amount of dsRNA generated by in vitro transcription of Cystic Fibrosis Transmembrane Conductance Regulator (CFTR) mRNA product by the Old Process (using T7 polymerase, lane 2) versus the New Process (using SP6 RNA Polymerase, lane 3) relative to a dsRNA control (lane 1).

Exemplary CFTR mRNA product generated by the Old Process contained significant amounts of double-stranded RNA while corresponding CFTR mRNA product generated by the New Process contained double-stranded RNA that was below the limit of detection (FIG. 4A).

Figure 4B:
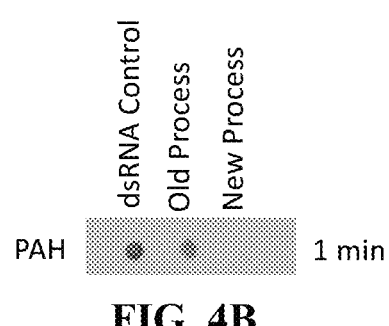
FIG. 4B is a dot blot showing a comparison of the amount of dsRNA generated by in vitro transcription of Phenylalanine Hydroxylase (PAH) mRNA product by the Old Process (using T7 polymerase, lane 2) versus the New Process (using SP6 RNA Polymerase, lane 3) relative to a dsRNA control (lane 1).

Similarly, exemplary PAH mRNA product generated by the Old Process contained significant amounts of double-stranded RNA, whereas the amount of double-stranded RNA in the corresponding PAH mRNA product generated by the New Process was below the limit of detection (FIG. 4B).

Figure 4C:
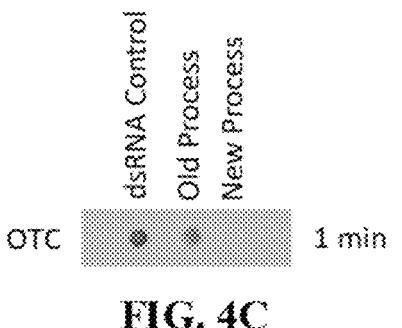
FIG. 4C is a dot blot showing a comparison of the amount of dsRNA generated by in vitro transcription of Ornithine Transcarbamoylase (OTC) mRNA product by the Old Process (using T7 polymerase, lane 2) versus the New Process (using SP6 RNA Polymerase, lane 3) relative to a dsRNA control (lane 1).

In addition, exemplary OTC mRNA product generated by the Old Process contained significant amounts of double-stranded RNA. In contrast, the amount of double-stranded RNA in the corresponding OTC mRNA product generated by the New Process was below the limit of detection (FIG. 4C).

This example demonstrates that SP6-mediated mRNA synthesis (New Process) may be scaled up to milligram quantities and yield mRNA product that is substantially free of dsRNA.

Example 4: Milligram Quantities of Both Modified and Unmodified mRNA Product Generated Using SP6 RNA Polymerase was Substantially Free of Double-Stranded RNA In this example, milligram quantities of HA mRNA were synthesized by in vitro transcription using SP6 RNA polymerase. In order to compare the amount of dsRNA present in the HA mRNA product comprising modified ribonucleotides, mRNA was synthesized in a single batch incorporating modified ribonucleotides into the polymerized transcript for comparison with mRNA synthesized incorporating native ribonucleotides.

In order to measure the amount of dsRNA, a dot blot was carried out. The blot was probed with an anti-dsRNA J2 monoclonal antibody and then incubated with secondary anti-mouse IgG horse radish peroxidase antibody. Signal detected from each of the samples after a one-minute exposure was compared to the signal obtained from a dsRNA control.

Figure 4D:
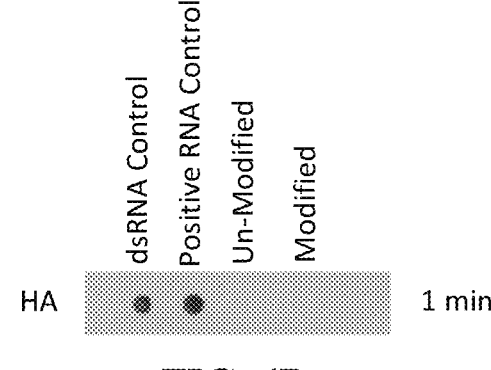
FIG. 4D is a dot blot showing a comparison of the amount of dsRNA generated by in vitro transcription of HA mRNA product using SP6 RNA Polymerase comprising unmodified (lane 3) versus modified ribonucleotides (lane 4) relative to a dsRNA control (lane 1). The dot also shows the mRNA product generated (lane 2).

The results showed that both modified and unmodified forms of HA mRNA product generated by in vitro transcription using SP6 RNA polymerase lacked substantial amounts of dsRNA (FIG. 4D).

This example demonstrates that SP6-mediated mRNA synthesis incorporating modified or unmodified ribonucleotides may be scaled up to milligram quantities and yield mRNA product that is substantially free of double-stranded RNA.

Example 5: Large-Scale mRNA Synthesis Using SP6 RNA Polymerase Generated 100 Gram Of mRNA Product that was Substantially Free of Double-Stranded RNA This example illustrates the amount of double-stranded RNA present in mRNA product generated in large-scale gram quantities. In this example, 100 grams of CFTR mRNA was produced in a single batch by in vitro transcription using SP6 RNA polymerase or T7 RNA polymerase.

In order to measure the amount of double-stranded RNA, a dot blot was carried out on mRNA product generated using SP6 RNA polymerase or T7 RNA polymerase. The blot was probed with an anti-dsRNA J2 monoclonal antibody and then incubated with secondary anti-mouse IgG horse radish peroxidase antibody. Signal detected from each of the samples after a one-minute exposure was compared to the signal obtained from a dsRNA control (FIG. 5, lane 1).

Figure 5:
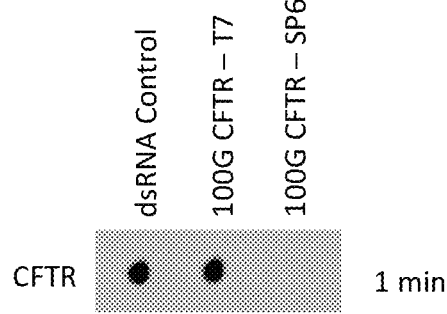
FIG. 5 is a dot blot showing a comparison of the amount of dsRNA present in 100 gram of CFTR mRNA product, generated by large-scale in vitro transcription using T7 polymerase (lane 2) versus SP6 polymerase (lane 3). The amount of dsRNA is quantified by comparison to a standard dsRNA control (lane 1).

The results showed that significant amounts of double-stranded RNA were produced in the T7 polymerase reaction (FIG. 5, lane 2) while the amount of double-stranded RNA produced in the SP6 RNA polymerase reaction was below the limit of detection (FIG. 5, lane 3).

This example demonstrates that SP6 RNA polymerase synthesis can be scaled up to meet commercial production of high quality mRNA product substantially free of double-stranded RNA.

Example 6: 250 mg mRNA Single Batch Synthesis Using SP6 RNA Polymerase was Substantially Free of Double-Stranded RNA This example illustrates the amount of double-stranded RNA present in mRNA product generated in large-scale gram quantities. In this example, 250 grams of CFTR mRNA was produced in a single batch by in vitro transcription using SP6 RNA polymerase.

Figures 6A, 6B:
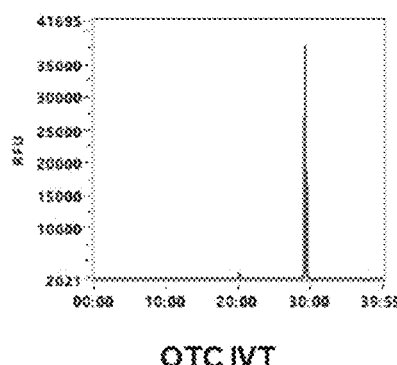
FIG. 6A is a series of graphs that show the tail length and integrity of OTC mRNA produced in a single batch yielding 250 mg using SP6 RNA polymerase.
FIG. 6B is a table that summarizes Cap analysis as assessed by UPLC-MS of OTC mRNA produced in a single batch yielding 250 mg.
Figure 6C:
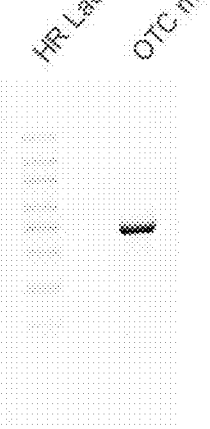
FIG. 6C depicts an agarose gel of SP6 OTC mRNA produced in a single batch yielding 250 mg.
Figure 6D:
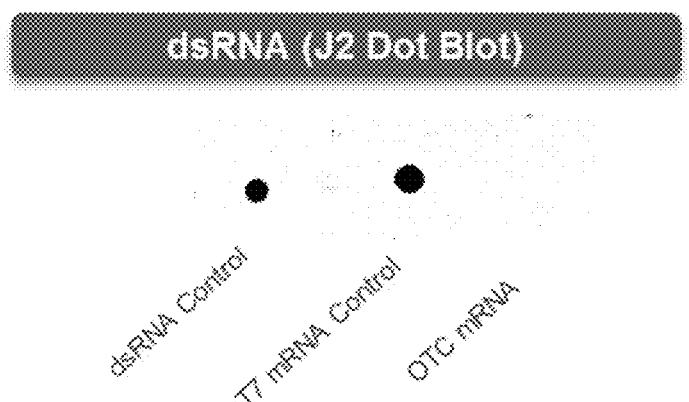
FIG. 6D depicts a dot blot to assess the presence of double-stranded RNA produced using either T7 RNA polymerase or SP6. A double stranded control lane is also shown.
Figure 6E:
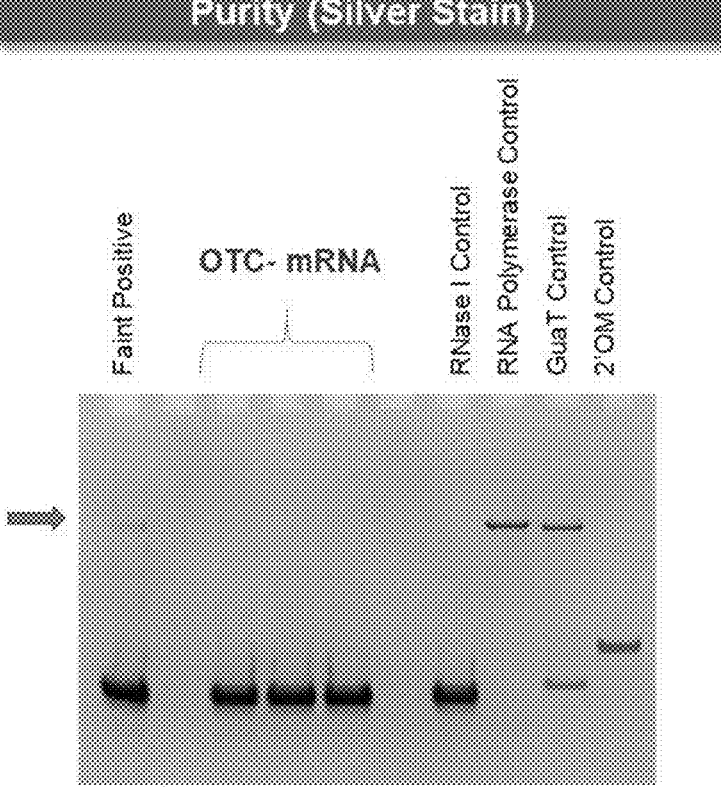
FIG. 6E depicts a silver staining gel that was used to assess the purity of OTC mRNA produced in a single batch using SP6 Polymerase yielding 250 mg.

250 mg of in vitro synthesized OTC mRNA produced in a single batch using SP6 RNA polymerase was analyzed for integrity by capillary electrophoresis (CE), mass spec, agarose gel analysis (FIG. 6A-6C). The in vitro synthesized mRNA was assessed for the presence of double stranded RNA (dsRNA) (FIG. 6D), and also was assessed for purity by silver staining (FIG. 6E). The data from these studies show that large scale mRNA synthesis produced using SP6 mRNA has high integrity and does not have any detectable double stranded RNA as assessed by dot blot (FIG. 6D). The OTC synthesized using SP6 polymerase also demonstrated high capping amounts as shown in FIG. 6B. Collectively, these data show improvements in terms of mRNA purity, reduction or elimination of detectable double stranded RNA, and high levels of RNA integrity obtained using SP6 RNA polymerase.

Example 7: Optimization of In Vitro Synthesis of mRNA Using SP6 RNA Polymerase Further studies were performed using SP6 RNA polymerase in order to optimize the in vitro mRNA synthesis conditions. For these studies, the amount of SP6 RNA polymerase was varied and the plasmid DNA (pDNA-DNA template) was also varied to ascertain the resultant effect following the variation of the concentration of these reagents on the yield of in vitro synthesized mRNA. The results and the conditions analyzed in these studies in summarized in Table 1 below.

TABLE 1

| Optimization Conditions Tested Using SP6 RNA Polymerase | | | |
|---|---|---|---|
| | Condition A | Condition B | Units |
| pDNA | 20 | 10 | mg/g RNA |
| SP6 | 10 | 20 | mg/g RNA |
| | Target | Actual | |
| Yield | 250 | 288 | grams |

As illustrated in Table 1, two concentrations of pDNA was tested: 1) 20 mg/g RNA, and 2) 10 mg/g RNA. Likewise, two concentrations of SP6 was tested: 1) 10 mg/g RNA; and 2) 20 mg/g RNA. The results show that increasing the amount of SP6 RNA polymerase used from 10 mg/g RNA to 20 mg/g RNA resulted in an mRNA yield of 288 grams. The results also show that increasing the pDNA concentration from 10 mg/g RNA to 20 mg/g RNA had a lower yield of 250 grams mRNA produced. These data show that increasing the concentration of SP6 RNA polymerase in the reaction resulted in a greater yield than that obtained by increasing the amount of pDNA used in the reaction. Specifically, increasing the concentration of SP6 RNA polymerase while maintaining a constant amount of pDNA resulted in increased yield.

Figure 7A:
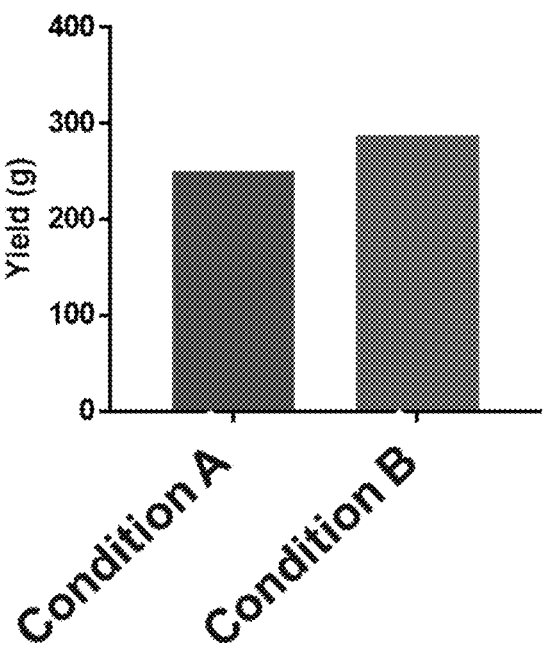
FIG. 7A-7C depict a series of graphs that show various data comparing "Condition A" and "Condition B" of SP6-produced OTC mRNA. For "Condition A" the following in vitro mRNA synthesis conditions were used: pDNA=20 mg/g RNA; SP6=10 mg/g RNA. For "Condition B" the following in vitro mRNA synthesis conditions were used: pDNA=10 mg/g RNA; and SP6=20 mg/g RNA.
Figure 7B:
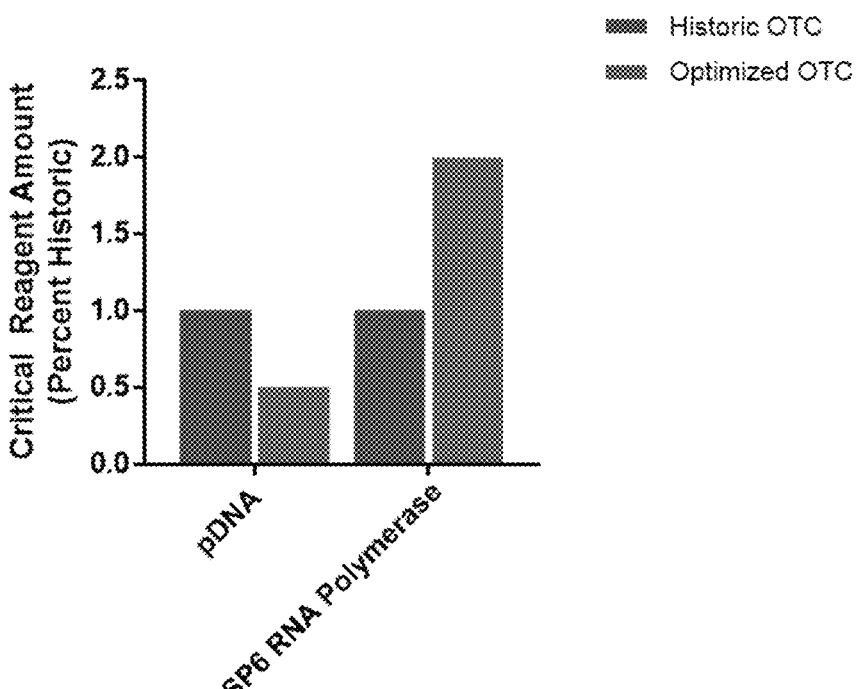
Figure 7C:
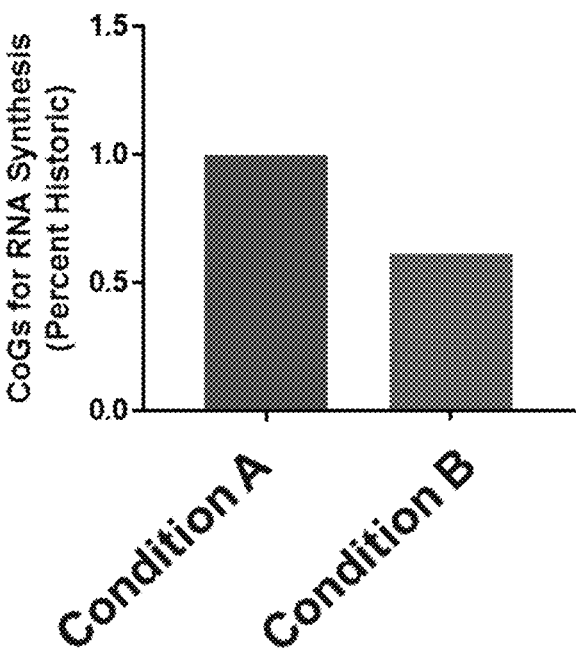

The results from these studies are illustrated graphically in FIGS. 7A, 7B and 7C, which show yield, critical reagent amount used and the Cost of Goods Produced (CoGS) for mRNA synthesized using SP6 RNA polymerase using the two conditions describe above and summarized in Table 1.

Example 8: In Vitro Synthesis of Modified mRNA Using SP6 RNA Polymerase

This example illustrates that modified mRNA product generated by in vitro transcription (IVT) using SP6 RNA polymerase was substantially free of both dsRNA and shortmer contamination.

mRNA was synthesized using a linearized double stranded DNA plasmid with an RNA polymerase-specific promoter, a suitable amount of SP6 RNA polymerase or T7 RNA polymerase, RNase inhibitor, pyrophosphatase, and NTPs comprising, e.g., 1-N-methyl-pseudouridine instead of uridine, and a suitable reaction buffer.

In two independent experiments, modified mRNA generated using SP6 RNA polymerase was substantially free of both dsRNA and shortmers. In comparison, modified mRNA generated using T7 RNA polymerase contained trace amounts of shortmers.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

---

What is claimed is:

1. A method of production of a composition comprising full-length messenger RNA (mRNA), comprising synthesizing in vitro mRNA from a DNA template using an SP6 RNA polymerase, wherein the mRNA is at least 500 bases in length, wherein the weight ratio of the DNA template to the SP6 RNA polymerase is between 1:1.5 and 1:2.5, wherein at least 100 mg of mRNA is synthesized in a single batch, and wherein the composition contains less than 1% of double-stranded RNA (dsRNA) by weight.

2. The method of claim 1, wherein the mRNA is synthesized at a non-denaturing condition.

3. The method of claim 1, wherein the in vitro synthesis of mRNA is performed in a buffer comprising 25 mM Tris HCl, 2 mM spermidine, 25 mM MgCl$_2$, 0.5 mM NaCl, and pH 7.5.

4. The method of claim 1, wherein the method further comprises a step of capping and/or tailing the synthesized mRNA.

5. The method of claim 1, wherein the method does not include a step of specifically removing the dsRNA.

6. The method of claim 1, wherein the SP6 RNA polymerase is a recombinant SP6 RNA polymerase.

7. The method of claim 1, wherein the DNA template comprises an SP6 promoter operably linked to a DNA sequence encoding the mRNA sequence to be synthesized.

8. The method of claim 7, wherein the DNA template sequence is optimized to reduce the chance of a hairpin structure forming in the synthesized mRNA.

9. The method of claim 1, wherein the mRNA is synthesized in a reaction mixture comprising NTPs at a concentration ranging from 1-10 mM for each NTP.

10. The method of claim 1, wherein the mRNA is synthesized at a temperature ranging from 37-42° C.

11. The method of claim 9, wherein the NTPs comprise modified NTPs.

12. The method of claim 1, wherein the weight ratio of the DNA template to the SP6 RNA polymerase is 1:1.5.

13. The method of claim 1, wherein the weight ratio of the DNA template to the SP6 RNA polymerase is about 1:2.

14. The method of claim 1, wherein the weight ratio of the DNA template to the SP6 RNA polymerase is 1:2.5.

15. The method of claim 11, wherein the modified NTPs comprise a modified uridine.

16. The method of claim 15, wherein the modified uridine is pseudouridine.

17. The method of claim 16, wherein the pseudouridine is N-1-methyl-pseudouridine.

18. The method of claim 1, wherein the DNA template is plasmid DNA.

19. The method of claim 1, wherein at least 10 mg of the DNA template is used to produce at least 1 gram of mRNA.

*   *   *   *   *

SEQUENCE LISTING

```
<160> NUMBER OF SEQ ID NOS: 18

<210> SEQ ID NO 1
<211> LENGTH: 874
<212> TYPE: PRT
<213> ORGANISM: Artificial Sequence
<220> FEATURE:
<223> OTHER INFORMATION: SP6 RNA polymerase (GenBank: Y00105.1)

<400> SEQUENCE: 1

Met Gln Asp Leu His Ala Ile Gln Leu Gln Leu Glu Glu Glu Met Phe
1               5                   10                  15

Asn Gly Gly Ile Arg Arg Phe Glu Ala Asp Gln Gln Arg Gln Ile Ala
                20                  25                  30

Ala Gly Ser Glu Ser Asp Thr Ala Trp Asn Arg Arg Leu Leu Ser Glu
            35                  40                  45

Leu Ile Ala Pro Met Ala Glu Gly Ile Gln Ala Tyr Lys Glu Glu Tyr
        50                  55                  60

Glu Gly Lys Lys Gly Arg Ala Pro Arg Ala Leu Ala Phe Leu Gln Cys
65                  70                  75                  80

Val Glu Asn Glu Val Ala Ala Tyr Ile Thr Met Lys Val Val Met Asp
                85                  90                  95

Met Leu Asn Thr Asp Ala Thr Leu Gln Ala Ile Ala Met Ser Val Ala
            100                 105                 110

Glu Arg Ile Glu Asp Gln Val Arg Phe Ser Lys Leu Glu Gly His Ala
            115                 120                 125

Ala Lys Tyr Phe Glu Lys Val Lys Lys Ser Leu Lys Ala Ser Arg Thr
        130                 135                 140

Lys Ser Tyr Arg His Ala His Asn Val Ala Val Val Ala Glu Lys Ser
145                 150                 155                 160

Val Ala Glu Lys Asp Ala Asp Phe Asp Arg Trp Glu Ala Trp Pro Lys
                165                 170                 175

Glu Thr Gln Leu Gln Ile Gly Thr Thr Leu Leu Glu Ile Leu Glu Gly
            180                 185                 190

Ser Val Phe Tyr Asn Gly Glu Pro Val Phe Met Arg Ala Met Arg Thr
        195                 200                 205

Tyr Gly Gly Lys Thr Ile Tyr Tyr Leu Gln Thr Ser Glu Ser Val Gly
```

-continued

```
        210                 215                 220

Gln Trp Ile Ser Ala Phe Lys Glu His Val Ala Gln Leu Ser Pro Ala
225                 230                 235                 240

Tyr Ala Pro Cys Val Ile Pro Pro Arg Pro Trp Arg Thr Pro Phe Asn
                245                 250                 255

Gly Gly Phe His Thr Glu Lys Val Ala Ser Arg Ile Arg Leu Val Lys
                260                 265                 270

Gly Asn Arg Glu His Val Arg Lys Leu Thr Gln Lys Gln Met Pro Lys
            275                 280                 285

Val Tyr Lys Ala Ile Asn Ala Leu Gln Asn Thr Gln Trp Gln Ile Asn
        290                 295                 300

Lys Asp Val Leu Ala Val Ile Glu Glu Val Ile Arg Leu Asp Leu Gly
305                 310                 315                 320

Tyr Gly Val Pro Ser Phe Lys Pro Leu Ile Asp Lys Glu Asn Lys Pro
                325                 330                 335

Ala Asn Pro Val Pro Val Glu Phe Gln His Leu Arg Gly Arg Glu Leu
                340                 345                 350

Lys Glu Met Leu Ser Pro Glu Gln Trp Gln Gln Phe Ile Asn Trp Lys
            355                 360                 365

Gly Glu Cys Ala Arg Leu Tyr Thr Ala Glu Thr Lys Arg Gly Ser Lys
        370                 375                 380

Ser Ala Ala Val Val Arg Met Val Gly Gln Ala Arg Lys Tyr Ser Ala
385                 390                 395                 400

Phe Glu Ser Ile Tyr Phe Val Tyr Ala Met Asp Ser Arg Ser Arg Val
                405                 410                 415

Tyr Val Gln Ser Ser Thr Leu Ser Pro Gln Ser Asn Asp Leu Gly Lys
            420                 425                 430

Ala Leu Leu Arg Phe Thr Glu Gly Arg Pro Val Asn Gly Val Glu Ala
            435                 440                 445

Leu Lys Trp Phe Cys Ile Asn Gly Ala Asn Leu Trp Gly Trp Asp Lys
        450                 455                 460

Lys Thr Phe Asp Val Arg Val Ser Asn Val Leu Asp Glu Glu Phe Gln
465                 470                 475                 480

Asp Met Cys Arg Asp Ile Ala Ala Asp Pro Leu Thr Phe Thr Gln Trp
                485                 490                 495

Ala Lys Ala Asp Ala Pro Tyr Glu Phe Leu Ala Trp Cys Phe Glu Tyr
            500                 505                 510

Ala Gln Tyr Leu Asp Leu Val Asp Glu Gly Arg Ala Asp Glu Phe Arg
            515                 520                 525

Thr His Leu Pro Val His Gln Asp Gly Ser Cys Ser Gly Ile Gln His
        530                 535                 540

Tyr Ser Ala Met Leu Arg Asp Glu Val Gly Ala Lys Ala Val Asn Leu
545                 550                 555                 560

Lys Pro Ser Asp Ala Pro Gln Asp Ile Tyr Gly Ala Val Ala Gln Val
                565                 570                 575

Val Ile Lys Lys Asn Ala Leu Tyr Met Asp Ala Asp Asp Ala Thr Thr
            580                 585                 590

Phe Thr Ser Gly Ser Val Thr Leu Ser Gly Thr Glu Leu Arg Ala Met
            595                 600                 605

Ala Ser Ala Trp Asp Ser Ile Gly Ile Thr Arg Ser Leu Thr Lys Lys
        610                 615                 620

Pro Val Met Thr Leu Pro Tyr Gly Ser Thr Arg Leu Thr Cys Arg Glu
625                 630                 635                 640
```

-continued

```
Ser Val Ile Asp Tyr Ile Val Asp Leu Glu Glu Lys Glu Ala Gln Lys
            645               650               655

Ala Val Ala Glu Gly Arg Thr Ala Asn Lys Val His Pro Phe Glu Asp
            660               665               670

Asp Arg Gln Asp Tyr Leu Thr Pro Gly Ala Ala Tyr Asn Tyr Met Thr
            675               680               685

Ala Leu Ile Trp Pro Ser Ile Ser Glu Val Val Lys Ala Pro Ile Val
        690               695               700

Ala Met Lys Met Ile Arg Gln Leu Ala Arg Phe Ala Ala Lys Arg Asn
705               710               715               720

Glu Gly Leu Met Tyr Thr Leu Pro Thr Gly Phe Ile Leu Glu Gln Lys
                725               730               735

Ile Met Ala Thr Glu Met Leu Arg Val Arg Thr Cys Leu Met Gly Asp
            740               745               750

Ile Lys Met Ser Leu Gln Val Glu Thr Asp Ile Val Asp Glu Ala Ala
            755               760               765

Met Met Gly Ala Ala Ala Pro Asn Phe Val His Gly His Asp Ala Ser
    770               775               780

His Leu Ile Leu Thr Val Cys Glu Leu Val Asp Lys Gly Val Thr Ser
785               790               795               800

Ile Ala Val Ile His Asp Ser Phe Gly Thr His Ala Asp Asn Thr Leu
            805               810               815

Thr Leu Arg Val Ala Leu Lys Gly Gln Met Val Ala Met Tyr Ile Asp
            820               825               830

Gly Asn Ala Leu Gln Lys Leu Leu Glu Glu His Glu Val Arg Trp Met
        835               840               845

Val Asp Thr Gly Ile Glu Val Pro Glu Gln Gly Glu Phe Asp Leu Asn
    850               855               860

Glu Ile Met Asp Ser Glu Tyr Val Phe Ala
865               870
```

```
<210> SEQ ID NO 2
<211> LENGTH: 2625
<212> TYPE: DNA
<213> ORGANISM: Artificial Sequence
<220> FEATURE:
<223> OTHER INFORMATION: SP6 RNA polymerase gene

<400> SEQUENCE: 2
atgcaagatt tacacgctat ccagcttcaa ttagaagaag agatgtttaa tggtggcatt      60
cgtcgcttcg aagcagatca acaacgccag attgcagcag gtagcgagag cgacacagca     120
tggaaccgcc gcctgttgtc agaacttatt gcacctatgg ctgaaggcat tcaggcttat     180
aaagaagagt acgaaggtaa gaaaggtcgt gcacctcgcg cattggcttt cttacaatgt     240
gtagaaaatg aagttgcagc atacatcact atgaaagttg ttatggatat gctgaatacg     300
gatgctaccc ttcaggctat tgcaatgagt gtagcagaac gcattgaaga ccaagtcgcg     360
ttttctaagc tagaaggtca cgccgctaaa tactttgaga aggttaagaa gtcactcaag     420
gctagccgta ctaagtcata tcgtcacgct cataacgtag ctgtagttgc tgaaaaatca     480
gttgcagaaa aggacgcgga ctttgaccgt tgggaggcgt ggccaaaaga aactcaattg     540
cagattggta ctaccttgct tgaaatctta gaaggtagcg ttttctataa tggtgaacct     600
gtatttatgc gtgctatgcg cacttatggc ggaaagacta tttactactt acaaacttct     660
gaaagtgtag gccagtggat tagcgcattc aaagagcacg tagcgcaatt aagcccagct     720
```

```
tatgcccctt gcgtaatccc tcctcgtcct tggagaactc catttaatgg agggttccat    780
actgagaagg tagctagccg tatccgtctt gtaaaaggta accgtgagca tgtacgcaag    840
ttgactcaaa agcaaatgcc aaaggtttat aaggctatca acgcattaca aaatacacaa    900
tggcaaatca acaaggatgt attagcagtt attgaagaag taatccgctt agaccttggt    960
tatggtgtac cttccttcaa gccactgatt gacaaggaga acaagccagc taacccggta   1020
cctgttgaat tccaacacct gcgcggtcgt gaactgaaag agatgctatc acctgagcag   1080
tggcaacaat tcattaactg gaaaggcgaa tgcgcgcgcc tatataccgc agaaactaag   1140
cgcggttcaa agtccgccgc cgttgttcgc atggtaggac aggcccgtaa atatagcgcc   1200
tttgaatcca tttacttcgt gtacgcaatg gatagccgca gccgtgtcta tgtgcaatct   1260
agcacgctct ctccgcagtc taacgactta ggtaaggcat tactccgctt taccgaggga   1320
cgccctgtga atggcgtaga agcgcttaaa tggttctgca tcaatggtgc taacctttgg   1380
ggatgggaca agaaaacttt tgatgtgcgc gtgtctaacg tattagatga ggaattccaa   1440
gatatgtgtc gagacatcgc cgcagaccct ctcacattca cccaatgggc taaagctgat   1500
gcaccttatg aattcctcgc ttggtgcttt gagtatgctc aataccttga tttggtggat   1560
gaaggaaggg ccgacgaatt ccgcactcac ctaccagtac atcaggacgg gtcttgttca   1620
ggcattcagc actatagtgc tatgcttcgc gacgaagtag gggccaaagc tgttaacctg   1680
aaaccctccg atgcaccgca ggatatctat ggggcggtgg cgcaagtggt tatcaagaag   1740
aatgcgctat atatggatgc ggacgatgca accacgttta cttctggtag cgtcacgctg   1800
tccggtacag aactgcgagc aatggctagc gcatgggata gtattggtat tacccgtagc   1860
ttaaccaaaa agcccgtgat gaccttgcca tatggttcta ctcgcttaac ttgccgtgaa   1920
tctgtgattg attacatcgt agacttagag gaaaaagagg cgcagaaggc agtagcagaa   1980
gggcggacgg caaacaaggt acatcctttt gaagacgatc gtcaagatta cttgactccg   2040
ggcgcagctt acaactacat gacggcacta atctggcctt ctatttctga agtagttaag   2100
gcaccgatag tagctatgaa gatgatacgc agcttgcac gctttgcagc gaaacgtaat   2160
gaaggcctga tgtacaccct gcctactggc ttcatcttag aacagaagat catggcaacc   2220
gagatgctac gcgtgcgtac ctgtctgatg ggtgatatca agatgtccct tcaggttgaa   2280
acggatatcg tagatgaagc cgctatgatg ggagcagcag cacctaattt cgtacacggt   2340
catgacgcaa gtcaccttat ccttaccgta tgtgaattgg tagacaaggg cgtaactagt   2400
atcgctgtaa tccacgactc ttttggtact catgcagaca acaccctcac tcttagagtg   2460
gcacttaaag ggcagatggt tgcaatgtat attgatggta atgcgcttca gaaactactg   2520
gaggagcatg aagtgcgctg gatggttgat acaggtatcg aagtacctga gcaaggggag   2580
ttcgacctta acgaaatcat ggattctgaa tacgtatttg cctaa                   2625

<210> SEQ ID NO 3
<211> LENGTH: 18
<212> TYPE: DNA
<213> ORGANISM: Artificial Sequence
<220> FEATURE:
<223> OTHER INFORMATION: SP6 promoter 1

<400> SEQUENCE: 3
atttaggtga cactatag                                                    18

<210> SEQ ID NO 4
```

-continued

```
<211> LENGTH: 23
<212> TYPE: DNA
<213> ORGANISM: Artificial Sequence
<220> FEATURE:
<223> OTHER INFORMATION: SP6 promoter 2

<400> SEQUENCE: 4 atttaggggga cactatagaa gag                                              23

<210> SEQ ID NO 5
<211> LENGTH: 22
<212> TYPE: DNA
<213> ORGANISM: Artificial Sequence
<220> FEATURE:
<223> OTHER INFORMATION: SP6 promoter 3

<400> SEQUENCE: 5 atttaggggga cactatagaa gg                                               22

<210> SEQ ID NO 6
<211> LENGTH: 23
<212> TYPE: DNA
<213> ORGANISM: Artificial Sequence
<220> FEATURE:
<223> OTHER INFORMATION: SP6 promoter 5

<400> SEQUENCE: 6 atttaggggga cactatagaa ggg                                              23

<210> SEQ ID NO 7
<211> LENGTH: 20
<212> TYPE: DNA
<213> ORGANISM: Artificial Sequence
<220> FEATURE:
<223> OTHER INFORMATION: SP6 promoter 5

<400> SEQUENCE: 7
atttaggtga cactatagaa                                                   20

<210> SEQ ID NO 8
<211> LENGTH: 22
<212> TYPE: DNA
<213> ORGANISM: Artificial Sequence
<220> FEATURE:
<223> OTHER INFORMATION: SP6 promoter 6

<400> SEQUENCE: 8
atttaggtga cactatagaa ga                                                22

<210> SEQ ID NO 9
<211> LENGTH: 23
<212> TYPE: DNA
<213> ORGANISM: Artificial Sequence
<220> FEATURE:
<223> OTHER INFORMATION: SP6 promoter 7

<400> SEQUENCE: 9
atttaggtga cactatagaa gag                                               23

<210> SEQ ID NO 10
<211> LENGTH: 22
<212> TYPE: DNA
<213> ORGANISM: Artificial Sequence
<220> FEATURE:
<223> OTHER INFORMATION: SP6 promoter 8

<400> SEQUENCE: 10
```

```
atttaggtga cactatagaa gg                                              22

<210> SEQ ID NO 11
<211> LENGTH: 23
<212> TYPE: DNA
<213> ORGANISM: Artificial Sequence
<220> FEATURE:
<223> OTHER INFORMATION: SP6 promoter 9

<400> SEQUENCE: 11
atttaggtga cactatagaa ggg                                             23

<210> SEQ ID NO 12
<211> LENGTH: 23
<212> TYPE: DNA
<213> ORGANISM: Artificial Sequence
<220> FEATURE:
<223> OTHER INFORMATION: SP6 promoter 10
<220> FEATURE:
<221> NAME/KEY: misc_feature
<222> LOCATION: (22)..(22)
<223> OTHER INFORMATION: n is a, c, g, or t

<400> SEQUENCE: 12
atttaggtga cactatagaa gng                                             23

<210> SEQ ID NO 13
<211> LENGTH: 24
<212> TYPE: DNA
<213> ORGANISM: Artificial Sequence
<220> FEATURE:
<223> OTHER INFORMATION: SP6 promoter 11

<400> SEQUENCE: 13
catacgattt aggtgacact atag                                            24

<210> SEQ ID NO 14
<211> LENGTH: 17
<212> TYPE: DNA
<213> ORGANISM: Artificial Sequence
<220> FEATURE:
<223> OTHER INFORMATION: process of dsRNA generation (a)

<400> SEQUENCE: 14
guagagguga agauuua                                                    17

<210> SEQ ID NO 15
<211> LENGTH: 15
<212> TYPE: DNA
<213> ORGANISM: Artificial Sequence
<220> FEATURE:
<223> OTHER INFORMATION: process of dsRNA generation (b) 1

<400> SEQUENCE: 15
gcugacugua ucuuc                                                      15

<210> SEQ ID NO 16
<211> LENGTH: 17
<212> TYPE: DNA
<213> ORGANISM: Artificial Sequence
<220> FEATURE:
<223> OTHER INFORMATION: process of dsRNA generation (b) 2

<400> SEQUENCE: 16
guagagguga agauuua                                                    17
```

```
<210> SEQ ID NO 17
<211> LENGTH: 20
<212> TYPE: DNA
<213> ORGANISM: Artificial Sequence
<220> FEATURE:
<223> OTHER INFORMATION: process of dsRNA generation (c) 1

<400> SEQUENCE: 17
guagagguga guaccguacg                                                    20

<210> SEQ ID NO 18
<211> LENGTH: 5
<212> TYPE: DNA
<213> ORGANISM: Artificial Sequence
<220> FEATURE:
<223> OTHER INFORMATION: process of dsRNA generation (c) 2

<400> SEQUENCE: 18 gguac                                                                    5
```